(12) United States Patent
McDaniel

(10) Patent No.: US 8,728,073 B2
(45) Date of Patent: May 20, 2014

(54) MULTI-REGION STAGED INFLATION BALLOON

(75) Inventor: Benjamin McDaniel, Irvine, CA (US)

(73) Assignee: Biosense Webster, Inc.

( * ) Notice: Subject to any disclaimer, the term of this patent is extended or adjusted under 35 U.S.C. 154(b) by 1696 days.

(21) Appl. No.: 11/539,935

(22) Filed: Oct. 10, 2006

(65) Prior Publication Data

US 2008/0086073 A1   Apr. 10, 2008

(51) Int. Cl.
*A61B 18/18* (2006.01)

(52) U.S. Cl.
USPC .............................................. 606/41; 606/45

(58) Field of Classification Search
USPC ............................ 606/41, 197; 600/115–116; 604/101.01–101.05, 103.06
See application file for complete search history.

(56) References Cited

U.S. PATENT DOCUMENTS

| | | | |
|---|---|---|---|
| 4,449,528 A | 5/1984 | Auth et al. | |
| 4,522,205 A | 6/1985 | Taylor et al. | |
| 4,569,801 A | 2/1986 | Molly et al. | |
| 4,641,649 A | 2/1987 | Walinsky et al. | |
| 4,662,368 A | 5/1987 | Hussein et al. | |
| 4,672,962 A | 6/1987 | Hershenson | |
| 4,673,563 A | 6/1987 | Berne et al. | |
| 4,676,258 A | 6/1987 | Inokuchi et al. | |
| 4,790,311 A | 12/1988 | Ruiz | |
| 4,807,620 A | 2/1989 | Strul et al. | |
| 4,898,591 A | 2/1990 | Jang et al. | |
| 4,998,933 A | 3/1991 | Eggers et al. | |
| 5,035,694 A | 7/1991 | Kasprzyk et al. | |
| 5,078,736 A | 1/1992 | Behl | |
| 5,104,393 A | 4/1992 | Isner et al. | |
| 5,178,618 A | 1/1993 | Kandarpa | |
| 5,190,540 A | 3/1993 | Lee | |

(Continued)

FOREIGN PATENT DOCUMENTS

WO   WO 93/20767 A1   10/1993
WO   WO 94/21165 A1   9/1994

(Continued)

OTHER PUBLICATIONS

Avitall, B., et al. "Physics and Engineering of Transcatheter Cardiac Tissue Ablation", JACC, vol. 22, No. 3 (1993) p. 921.

(Continued)

*Primary Examiner* — Linda Dvorak
*Assistant Examiner* — Amanda Scott

(57) ABSTRACT

The present invention involves a surgical device and method of use, particularly an assembly and method incorporating a shaped expandable member along the distal region of an ablation device to facilitate ablation of a circumferential region of tissue engaged by the expandable member. The ablation device assembly includes an elongate body with a proximal end portion, a distal end portion, and a longitudinal axis. A contact member is located along the distal end portion of the elongate body. The contact member has a circumferential wall and is expandable from a radially collapsed condition to a radially expanded condition. The contact member also includes a single chamber having a single bulbous section. The single bulbous section has a plurality of longitudinally adjacent circumferential regions wherein adjacent regions have dissimilar wall thicknesses. The ablation device also has an ablation element having an ablative energy source that is located along the distal end portion, wherein the ablation element cooperates with the contact member such that the ablative energy source emits a substantially circumferential pattern of energy through the circumferential wall.

22 Claims, 17 Drawing Sheets

(56) References Cited

U.S. PATENT DOCUMENTS

| | | |
|---|---|---|
| 5,226,430 A | 7/1993 | Spears et al. |
| 5,292,321 A | 3/1994 | Lee |
| 5,348,554 A | 9/1994 | Imran et al. |
| 5,423,811 A | 6/1995 | Imran et al. |
| 5,427,119 A | 6/1995 | Swartz et al. |
| 5,449,380 A | 9/1995 | Chin |
| 5,487,385 A | 1/1996 | Avitall |
| 5,497,119 A | 3/1996 | Tedrow et al. |
| 5,505,730 A | 4/1996 | Edwards |
| 5,545,161 A | 8/1996 | Imran |
| 5,545,193 A | 8/1996 | Fleischman et al. |
| 5,549,661 A | 8/1996 | Kordis et al. |
| 5,558,672 A | 9/1996 | Edwards et al. |
| 5,562,720 A | 10/1996 | Stern et al. |
| 5,564,440 A | 10/1996 | Swartz et al. |
| 5,569,241 A | 10/1996 | Edwards |
| 5,575,766 A | 11/1996 | Swartz et al. |
| 5,575,788 A | 11/1996 | Baker et al. |
| 5,575,810 A | 11/1996 | Swanson et al. |
| 5,582,609 A | 12/1996 | Swanson et al. |
| 5,606,974 A | 3/1997 | Castellano et al. |
| 5,617,854 A | 4/1997 | Munsif |
| 5,620,479 A | 4/1997 | Diederich |
| 5,658,278 A | 8/1997 | Imran et al. |
| 5,687,723 A | 11/1997 | Avitall |
| 5,688,267 A | 11/1997 | Panescu et al. |
| 5,697,927 A | 12/1997 | Imran et al. |
| 5,702,438 A | 12/1997 | Avitall |
| 5,722,403 A | 3/1998 | McGee et al. |
| 5,733,301 A * | 3/1998 | Forman .......... 606/192 |
| 5,769,846 A | 6/1998 | Edwards et al. |
| 5,938,660 A | 8/1999 | Swartz et al. |
| 5,971,983 A | 10/1999 | Lesh |
| 6,012,457 A | 1/2000 | Lesh |
| 6,024,740 A | 2/2000 | Lesh et al. |
| 6,117,101 A | 9/2000 | Diederich et al. |
| 6,193,738 B1 * | 2/2001 | Tomaschko et al. ......... 606/194 |
| 6,500,174 B1 * | 12/2002 | Maguire et al. ......... 606/41 |
| 6,522,930 B1 | 2/2003 | Schaer et al. |
| 6,527,769 B2 | 3/2003 | Langberg et al. |
| 6,652,515 B1 | 11/2003 | Maguire et al. |
| 2002/0165535 A1 * | 11/2002 | Lesh et al. ............ 606/41 |
| 2005/0065504 A1 * | 3/2005 | Melsky et al. ............ 606/16 |

FOREIGN PATENT DOCUMENTS

| | | |
|---|---|---|
| WO | WO 96/10961 A1 | 4/1996 |
| WO | WO 96/26675 A1 | 9/1996 |
| WO | WO 96/32897 A1 | 10/1996 |
| WO | WO 97/32525 A1 | 9/1997 |
| WO | WO 97/37607 A2 | 10/1997 |
| WO | WO 98/02201 A1 | 1/1998 |
| WO | WO 99/00064 A1 | 1/1999 |
| WO | WO 99/02096 A1 | 1/1999 |

OTHER PUBLICATIONS

Cox, J., et al. "The Surgical Treatment of Atrial Fibrillation. I. Summary of the current Concepts of the Mechanisms of Atrial Flutter and Atrial Fibrillation", J. Thorac Cardiovasc Surgery, vol. 101 (1991) p. 403-405.

Cox, J., et al. "The Surgical Treatment of Atrial Fibrillation. IV. Surgical Technique", J. Thorac Cardiovasc. Surgery, vol. 101 (1993), p. 584-92.

Fram, D., et al. "Feasibility of radiofrequency Powered, Thermal Balloon Ablation of Atrioventricular bypass Tracts Via the Coronary Sinus: In Vivo Canine Studies", PACE, vol. 18 (1995), p. 1518.

Haissagueree, M., et al. "Right and Left Atrial radiofrequency Catheter Therapy of Paroxysmal Atrial Fibrillation", J. Cardiovasc. Electrophysiol. vol. 7 (1996) p. 1132-1144.

Jais, P., et al. A Focal Source of Atrial Fibrillation Treated by Discrete Radiofrequency Ablation, Circulation vol. 95(3) (1997) p. 572-576.

McMath, L., et al. "Percutaneous Laser Balloon Coagulation of Accessory Pathways", Diagnostic and Therapeutic Cardiovascular Interventions vol. 1425 (1991) p. 165.

Schuger, C., et al. "Long-Term Effects of Percutaneous Laser Balloon Ablation From the Canine Coronary Sinus", Circulation vol. 86 (1992) p. 947-954.

Sueda, T., et al. "Simple Left Atrial Procedure for Chronic Atrial Fibrillation Associated with Mitral Valve Disease", Ann Thorac Surgery vol. 62 (1996) p. 1796-800.

* cited by examiner

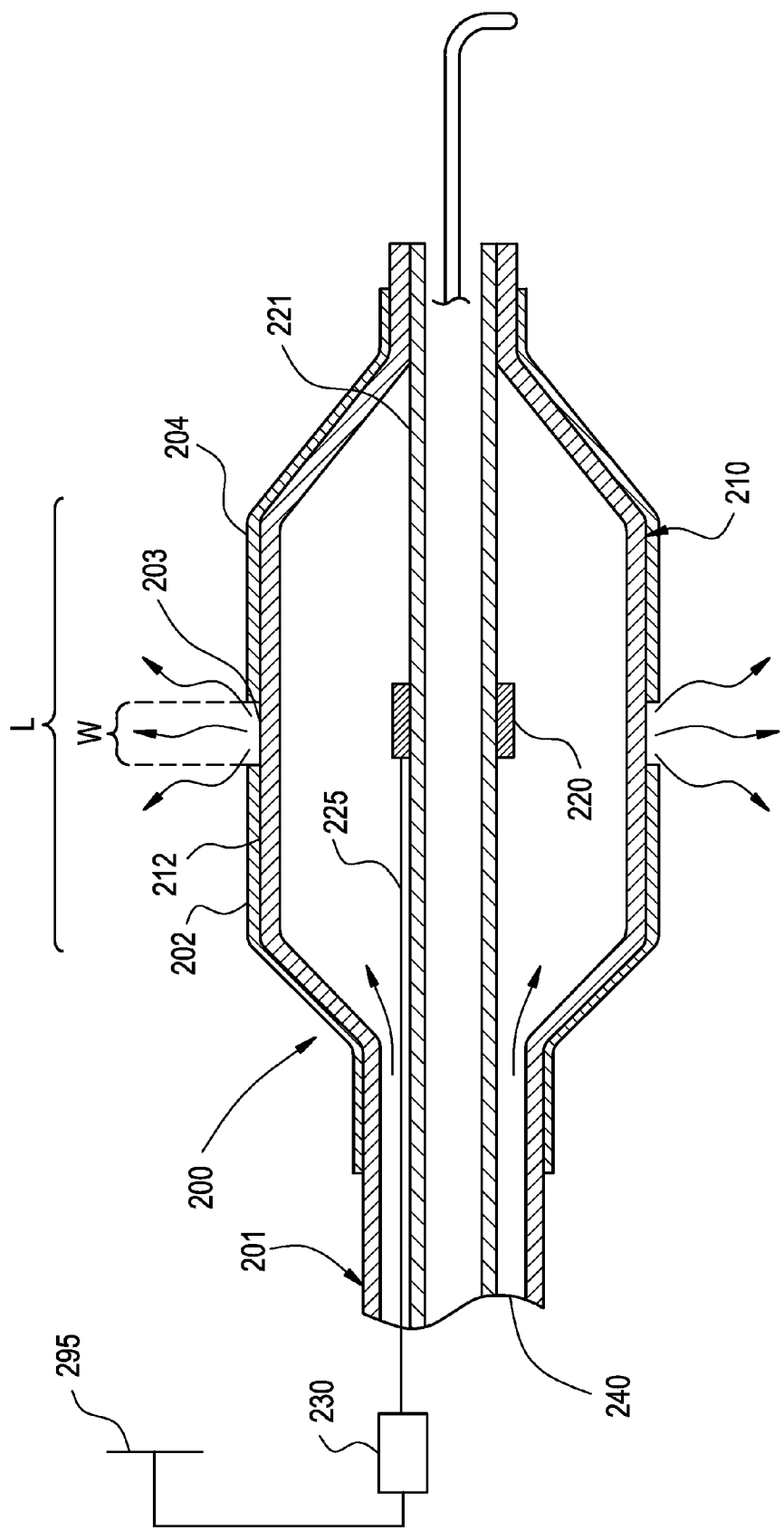

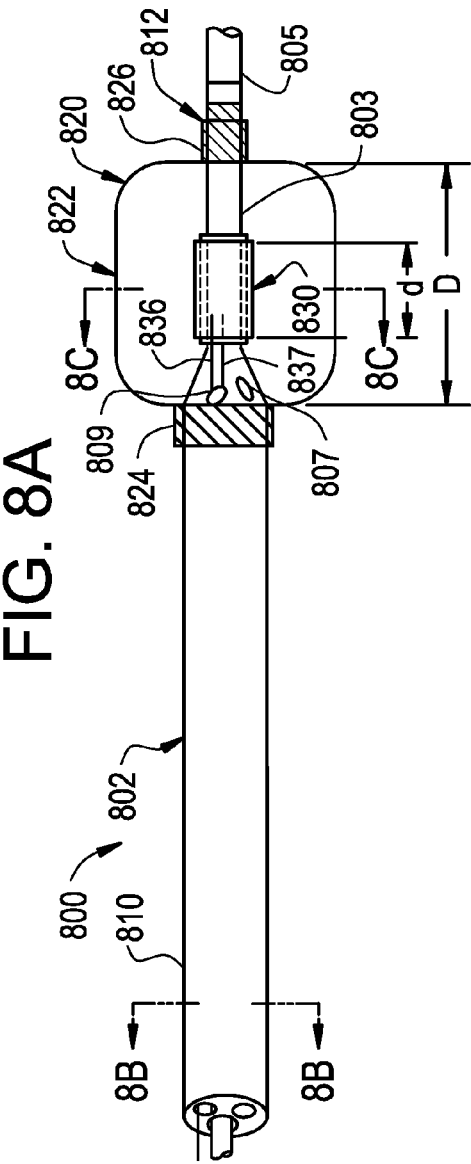
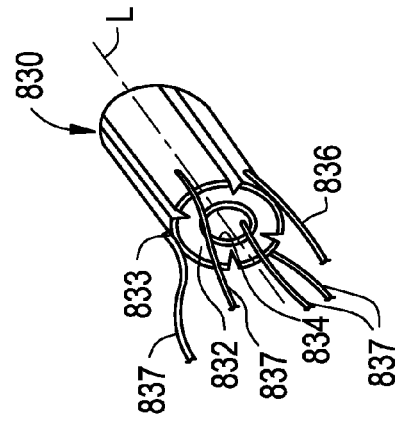
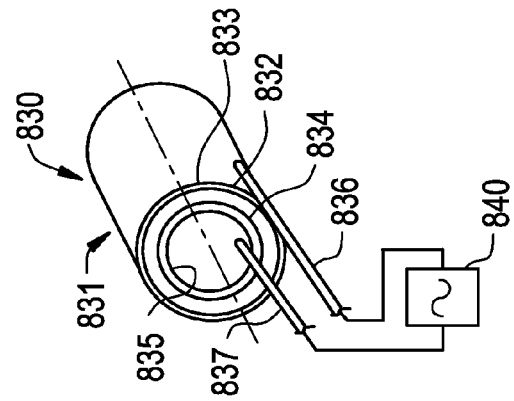
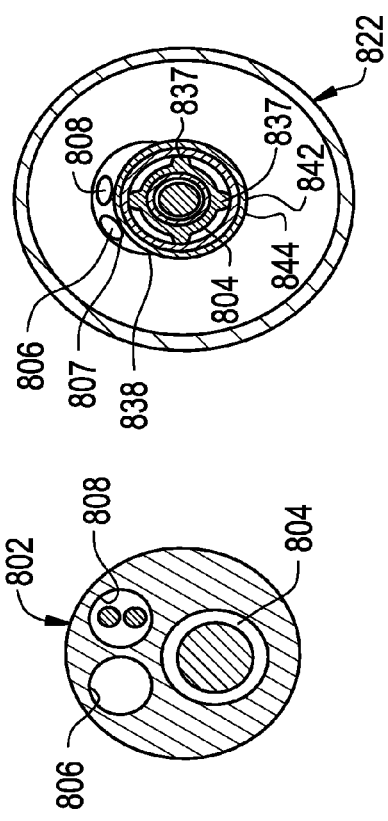
FIG. 8A
FIG. 8B
FIG. 8C
FIG. 8D
FIG. 8E

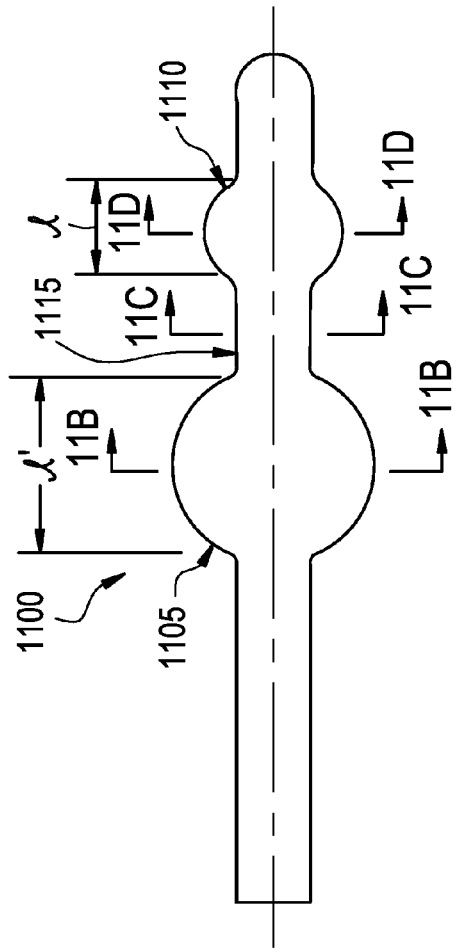
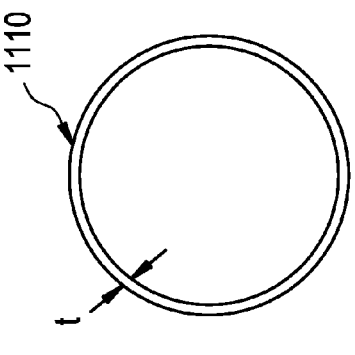
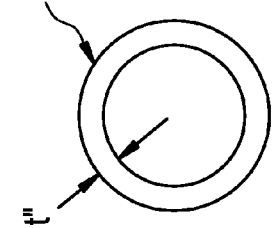
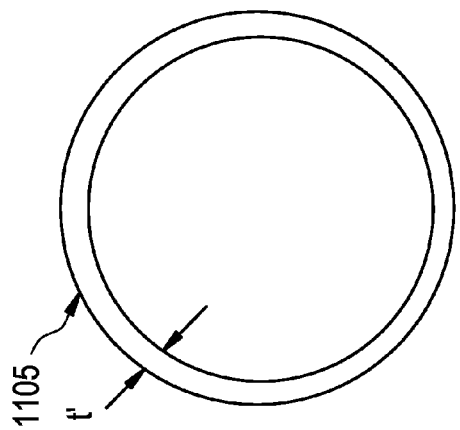

MULTI-REGION STAGED INFLATION BALLOON

FIELD OF THE INVENTION

The present invention involves a surgical device and method of use. Specifically, it involves a circumferential ablation device assembly and associated methods of use. One aspect of the present invention specifically involves an assembly and method incorporating a shaped expandable member along the distal region of an ablation device, where the expandable member has different regions with different physical or mechanical properties.

BACKGROUND

The terms "body space," including derivatives thereof, is herein intended to mean any cavity or lumen within the body that is defined at least in part by a tissue wall. For example, the cardiac chambers, the uterus, the regions of the gastrointestinal tract, and the arterial or venous vessels are all considered illustrative examples of body spaces within the intended meaning.

The term "body lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

Many local energy delivery devices and methods have been developed for treating the various abnormal tissue conditions in the body, and particularly for treating abnormal tissue along body space walls which define various body spaces in the body. For example, various devices have been disclosed with the primary purpose of treating or recanalizing atherosclerotic vessels with localized energy delivery. Several prior devices and methods combine energy delivery assemblies in combination with cardiovascular stent devices in order to locally deliver energy to tissue in order to maintain patency in diseased lumens such as blood vessels. Endometriosis, another abnormal wall tissue condition that is associated with the endometrial cavity and is characterized by dangerously proliferative uterine wall tissue along the surface of the endometrial cavity, has also been treated by local energy delivery devices and methods. Several other devices and methods have also been disclosed which use catheter-based heat sources for the intended purpose of inducing thrombosis and controlling hemorrhaging within certain body lumens such as vessels. Detailed examples of local energy delivery devices and related procedures such as those of the types just described above are variously disclosed in the following references: U.S. Pat. No. 4,672,962 to Hershenson; U.S. Pat. No. 4,676,258 to InoKuchi et al.; U.S. Pat. No. 4,790,311 to Ruiz; U.S. Pat. No. 4,807,620 to Strul et al.; U.S. Pat. No. 4,998,933 to Eggers et al.; U.S. Pat. No. 5,035,694 to Kasprzyk et al.; U.S. Pat. No. 5,190,540 to Lee; U.S. Pat. No. 5,226,430 to Spears et al.; and U.S. Pat. No. 5,292,321 to Lee; U.S. Pat. No. 5,449,380 to Chin; U.S. Pat. No. 5,505,730 to Edwards; U.S. Pat. No. 5,558,672 to Edwards et al.; and U.S. Pat. No. 5,562,720 to Stern et al.; U.S. Pat. No. 4,449,528 to Auth et al.; U.S. Pat. No. 4,522,205 to Taylor et al.; and U.S. Pat. No. 4,662,368 to Hussein et al.; U.S. Pat. No. 5,078,736 to Behl; and U.S. Pat. No. 5,178,618 to Kandarpa. The disclosures of these references are herein incorporated in their entirety by reference thereto.

Other prior devices and methods electrically couple fluid to an ablation element during local energy delivery for treatment of abnormal tissues. Some such devices couple the fluid to the ablation element for the primary purpose of controlling the temperature of the element during the energy delivery. Other such devices couple the fluid more directly to the tissue-device interface either as another temperature control mechanism or in certain other known applications as a carrier or medium for the localized energy delivery, itself. More detailed examples of ablation devices which use fluid to assist in electrically coupling electrodes to tissue are disclosed in the following references: U.S. Pat. No. 5,348,554 to Imran et al.; U.S. Pat. No. 5,423,811 to Imran et al.; U.S. Pat. No. 5,505,730 to Edwards; U.S. Pat. No. 5,545,161 to Imran et al.; U.S. Pat. No. 5,558,672 to Edwards et al.; U.S. Pat. No. 5,569,241 to Edwards; U.S. Pat. No. 5,575,788 to Baker et al.; U.S. Pat. No. 5,658,278 to Imran et al.; U.S. Pat. No. 5,688,267 to Panescu et al.; U.S. Pat. No. 5,697,927 to Imran et al.; U.S. Pat. No. 5,722,403 to McGee et al.; U.S. Pat. No. 5,769,846; and PCT Patent Application Publication No. WO 97/32525 to Pomeranz et al.; and PCT Patent Application Publication No. WO 98/02201 to Pomeranz et al. To the extent not previously incorporated above, the disclosures of these references are herein incorporated in their entirety by reference thereto.

Atrial Fibrillation

Cardiac arrhythmias, and atrial fibrillation in particular, persist as common and dangerous medical ailments associated with abnormal cardiac chamber wall tissue, and has been observed especially in the aging population. In patients with cardiac arrhythmia, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion. Cardiac arrhythmias, including atrial fibrillation, may be generally detected using the global technique of an electrocardiogram (EKG). More sensitive procedures of mapping the specific conduction along the cardiac chambers have also been disclosed, such as, for example, in U.S. Pat. No. 4,641,649 to Walinsky et al. and Published PCT Patent Application No. WO 96/32897 to Desai. The disclosures of these references are herein incorporated in their entirety by reference thereto.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Several pharmacological approaches intended to remedy or otherwise treat atrial arrhythmias have been disclosed, such as for example according to the disclosures of the following references: U.S. Pat. No. 4,673,563 to Berne et al.; U.S. Pat. No. 4,569,801 to Molloy et al.; and also "Current Management of Arrhythmias" (1991) by Hindricks, et al. However, such pharmacological solutions are not generally believed to be entirely effective in many cases, and are even believed in some cases to result in proarrhythmia and long term inefficacy. The disclosures of these references are herein incorporated in their entirety by reference thereto.

Several surgical approaches have also been developed with the intention of treating atrial fibrillation. One particular example is known as the "Maze procedure," as is disclosed by Cox, J L et al. in "The surgical treatment of atrial fibrillation. I. Summary" *Thoracic and Cardiovascular Surgery* 101(3), pp. 402-405 (1991); and also by Cox, J L in "The surgical treatment of atrial fibrillation. IV. Surgical Technique", *Thoracic and Cardiovascular Surgery* 101(4), pp. 584-592 (1991). In general, the "Maze" procedure is designed to relieve atrial arrhythmia by restoring effective atrial systole and sinus node control through a prescribed pattern of incisions about the tissue wall. In the early clinical experiences reported, the "Maze" procedure included surgical incisions in both the right and the left atrial chambers. However, more recent reports predict that the surgical "Maze" procedure may be substantially efficacious when performed only in the left atrium, such as is disclosed in Sueda et al., "Simple Left Atrial Procedure for Chronic Atrial Fibrillation Associated With Mitral Valve Disease" (1996). The disclosure of these cited references are herein incorporated in their entirety by reference thereto.

The "Maze procedure" as performed in the left atrium generally includes forming vertical incisions from the two superior pulmonary veins and terminating in the region of the mitral valve annulus, traversing the region of the inferior pulmonary veins en route. An additional horizontal line also connects the superior ends of the two vertical incisions. Thus, the atrial wall region bordered by the pulmonary vein ostia is isolated from the other atrial tissue. In this process, the mechanical sectioning of atrial tissue eliminates the arrhythmogenic conduction from the boxed region of the pulmonary veins and to the rest of the atrium by creating conduction blocks within the aberrant electrical conduction pathways. Other variations or modifications of this specific pattern just described have also been disclosed, all sharing the primary purpose of isolating known or suspected regions of arrhythmogenic origin or propagation along the atrial wall.

While the "Maze" procedure and its variations as reported by Cox and others have met some success in treating patients with atrial arrhythmia, its highly invasive methodology is believed to be prohibitive in most cases. However, these procedures have provided a guiding principle that electrically isolating faulty cardiac tissue may successfully prevent atrial arrhythmia, and particularly atrial fibrillation caused by arrhythmogenic conduction arising from the region of the pulmonary veins.

Less invasive catheter-based approaches to treat atrial fibrillation have been disclosed which implement cardiac tissue ablation for terminating arrhythmogenic conduction in the atria. Examples of such catheter-based devices and treatment methods have generally targeted atrial segmentation with ablation catheter devices and methods adapted to form linear or curvilinear lesions in the wall tissue that defines the atrial chambers. Some specifically disclosed approaches provide specific ablation elements that are linear over a defined length intended to engage the tissue for creating the linear lesion. Other disclosed approaches provide shaped or steerable guiding sheaths, or sheaths within sheaths, for the intended purpose of directing tip ablation catheters toward the posterior left atrial wall such that sequential ablations along the predetermined path of tissue may create the desired lesion. In addition, various energy delivery modalities have been disclosed for forming atrial wall lesions, and include use of microwave, laser, ultrasound, thermal conduction, and more commonly, radiofrequency energies to create conduction blocks along the cardiac tissue wall.

Further more detailed examples of ablation device assemblies and methods for creating lesions along an atrial wall are disclosed in the following U.S. Patent references: U.S. Pat. No. 4,898,591 to Jang et al.; U.S. Pat. No. 5,104,393 to Isner et al.; U.S. Pat. No. 5,427,119; U.S. Pat. No. 5,487,385 to Avitall; U.S. Pat. No. 5,497,119 to Swartz et al.; U.S. Pat. No. 5,545,193 to Fleischman et al.; U.S. Pat. No. 5,549,661 to Kordis et al.; U.S. Pat. No. 5,575,810 to Swanson et al.; U.S. Pat. No. 5,564,440 to Swartz et al.; U.S. Pat. No. 5,592,609 to Swanson et al.; U.S. Pat. No. 5,575,766 to Swartz et al.; U.S. Pat. No. 5,582,609 to Swanson; U.S. Pat. No. 5,617,854 to Munsif, U.S. Pat. No. 5,687,723 to Avitall; U.S. Pat. No. 5,702,438 to Avitall. To the extent not previously incorporated above, the disclosures of these references are herein incorporated in their entirety by reference thereto.

Other examples of such ablation devices and methods are disclosed in the following Published PCT Patent Applications: WO 93/20767 to Stem et al.; WO 94/21165 to Kordis et al.; WO 96/10961 to Fleischman et al.; WO 96/26675 to Klein et al.; and WO 97/37607 to Schaer. To the extent not previously incorporated above, the disclosures of these references are herein incorporated in their entirety by reference thereto.

Additional examples of such ablation devices and methods are disclosed in the following published articles: "Physics and Engineering of Transcatheter Tissue Ablation", Avitall et al., *Journal of American College of Cardiology*, Volume 22, No. 3:921-932 (1993); and "Right and Left Atrial Radiofrequency Catheter Therapy of Paroxysmal Atrial Fibrillation," Haissaguerre, et al., *Journal of Cardiovascular Electrophysiology* 7(12), pp. 1132-1144 (1996). The disclosures of these references are herein incorporated in their entirety by reference thereto.

In addition to those known assemblies just summarized above, additional tissue ablation device assemblies have also been recently developed for the specific purpose of ensuring firm contact and consistent positioning of a linear ablation element along a length of tissue by anchoring the element at least at one predetermined location along that length, such as in order to form a "Maze"-type lesion pattern in the left atrium. One example of such assemblies includes an anchor at each of two ends of a linear ablation element in order to secure those ends to each of two predetermined locations along a left atrial wall, such as at two adjacent pulmonary veins, so that tissue may be ablated along the length of tissue extending therebetween.

In addition to attempting atrial wall segmentation with long linear lesions for treating atrial arrhythmia, other ablation device and method have also been disclosed which are intended to use expandable members such as balloons to ablate cardiac tissue. Some such devices have been disclosed primarily for use in ablating tissue wall regions along the cardiac chambers. Other devices and methods have been disclosed for treating abnormal conduction of the left-sided accessory pathways, and in particular associated with "Wolff-Parkinson-White" syndrome—various such disclosures use a balloon for ablating from within a region of an associated coronary sinus adjacent to the desired cardiac tissue to ablate. Further more detailed examples of devices and methods such as of the types just described are variously disclosed in the following published references: Fram et al., in "Feasibility of RF Powered Thermal Balloon Ablation of Atrioventricular Bypass Tracts via the Coronary Sinus: In vivo Canine Studies," *PACE*, Vol. 18, p 1518-1530 (1995); "Long-term effects of percutaneous laser balloon ablation from the canine coronary sinus", Schuger CD et al., *Circulation* (1992) 86:947-954; and "Percutaneous laser balloon coagulation of accessory pathways", McMath L P et al., *Diagn Ther Cardiovasc Interven* 1991; 1425:165-171. The disclosures of these references are herein incorporated in their entirety by reference thereto.

Arrhythmias Originating from Foci in Pulmonary Veins

Various modes of atrial fibrillation have also been observed to be focal in nature, caused by the rapid and repetitive firing of an isolated center within cardiac muscle tissue associated with the atrium. Such foci may act as either a trigger of atrial fibrillatory paroxysmal or may even sustain the fibrillation. Various disclosures have suggested that focal atrial arrhythmia often originates from at least one tissue region along one or more of the pulmonary veins of the left atrium, and even more particularly in the superior pulmonary veins.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to terminate the inappropriate arrhythmogenic conduction.

One example of a focal ablation method intended to treat focal arrhythmia originating from a pulmonary vein is disclosed by Haissaguerre, et al. in "Right and Left Atrial Radiofrequency Catheter Therapy of Paroxysmal Atrial Fibrillation" in *Journal of Cardiovascular Electrophysiology* 7(12), pp. 1132-1144 (1996) (previously incorporated by reference above). Haissaguerre, et al. discloses radiofrequency catheter ablation of drug-refractory paroxysmal atrial fibrillation using linear atrial lesions complemented by focal ablation targeted at arrhythmogenic foci in a screened patient population. The site of the arrhythmogenic foci were generally located just inside the superior pulmonary vein, and the focal ablations were generally performed using a standard 4 mm tip single ablation electrode.

Another focal ablation method of treating atrial arrhythmias is disclosed in Jais et al., "A focal source of atrial fibrillation treated by discrete radiofrequency ablation," *Circulation* 95:572-576 (1997). The disclosure of this reference is herein incorporated in its entirety by reference thereto. Jais et al. discloses treating patients with paroxysmal arrhythmias originating from a focal source by ablating that source. At the site of arrhythmogenic tissue, in both right and left atria, several pulses of a discrete source of radiofrequency energy were applied in order to eliminate the fibrillatory process.

Other assemblies and methods have been disclosed addressing focal sources of arrhythmia in pulmonary veins by ablating circumferential regions of tissue either along the pulmonary vein, at the ostium of the vein along the atrial wall, or encircling the ostium and along the atrial wall. More detailed examples of device assemblies and methods for treating focal arrhythmia as just described are disclosed in Published PCT Patent Application No. WO 99/02096 to Diederich et al., and also in the following U.S. patents: U.S. Pat. No. 6,024,740 for "Circumferential Ablation Device Assembly" to Michael D. Lesh et al., on Feb. 15, 2000; U.S. Pat. No. 6,012,457 for "Device and Method for Forming a Circumferential Conduction Block in a Pulmonary Vein" to Michael D. Lesh, on Jan. 11, 2000; and U.S. Pat. No. 6,117,101 for "Circumferential Ablation Device Assembly" to Chris J. Diederich et al., on Sep. 12, 2000.

Another specific device assembly and method which is intended to treat focal atrial fibrillation by ablating a circumferential region of tissue between two seals in order to form a conduction block to isolate an arrhythmogenic focus within a pulmonary vein is disclosed in U.S. Pat. No. 5,938,660 and a related Published PCT Patent Application No. WO 99/00064. The disclosures of these references are herein incorporated in their entirety by reference thereto.

SUMMARY OF THE INVENTION

It is an object of the invention to provide a circumferential ablation device assembly, and related method of use, which ablates a circumferential region of tissue at a location where a pulmonary vein extends from an atrium, including along the atrial wall. The ablation device comprises an elongate body with a proximal end portion, a distal end portion, and a longitudinal axis. An elastic contact member is located along the distal end portion, the contact member having a circumferential wall and being expandable from a radially collapsed condition to a radially expanded condition. The contact member includes a single chamber having a single bulbous section, wherein the single bulbous section has a plurality of longitudinally adjacent circumferential regions such that adjacent regions have dissimilar wall thicknesses. The ablation device further includes an ablation element having an ablative energy source that is located along the distal end portion and cooperates with the contact member such that the ablative energy source emits a substantially circumferential pattern of energy through the circumferential wall.

Another embodiment of the present invention includes an elastic contact member having a circumferential wall. The elastic contact member is expandable from a radially collapsed condition to a radially expanded condition. The contact member includes a single chamber having a single bulbous section, wherein the single bulbous section has a plurality of longitudinally adjacent circumferential regions. The adjacent regions have dissimilar tensile strengths.

Still another embodiment of the invention includes an expandable member for use in an ablation device. The expandable member comprises a single chamber having a single bulbous section. The single bulbous section has a plurality of longitudinally adjacent circumferential regions wherein the adjacent circumferential regions commence elastic expansion at different points in time.

BRIEF DESCRIPTION OF THE DRAWINGS

FIG. 2 shows a longitudinal cross-sectional view of one type of circumferential ablation device with a balloon ablation member that is secured to the distal end of an over-the-wire catheter and that has a working length with a circumferential, ablative band disposed between two insulated and non-ablative end portions.

FIG. 8A shows a longitudinal cross-sectional view of another circumferential ablation catheter with an ablation element having a single cylindrical ultrasound transducer that is positioned along an inner member within an expandable balloon that is further shown in a radially expanded condition.

FIG. 8B shows a transverse cross-sectional view of the circumferential ablation catheter shown in FIG. 8A taken along line 8B-8B shown in FIG. 8A.

FIG. 8C shows a transverse cross-sectional view of the circumferential ablation catheter shown in FIG. 8A taken along line 8C-8C shown in FIG. 8A.

FIG. 8D shows a perspective view of the ultrasonic transducer of FIG. 8A in isolation.

FIG. 8E shows a modified version of the ultrasonic transducer of FIG. 8D with individually driven sectors.

FIGS. 11A-D shows a further barbell shape for an expandable member according to the tissue ablation devices and procedures according to the invention.

DETAILED DESCRIPTION OF PARTICULAR EMBODIMENTS

Particular Definitions

Various terms are defined throughout this specification, and the meaning of any particular term is to be understood in the context of this entire document, in addition to the context of a particular description or use given in a specific circumstance as described hereunder. Various such terms are to be understood as follows:

The terms "circumference" or "circumferential", including derivatives thereof, are herein intended to mean a substantially continuous path or line that forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, is herein intended to mean to substantially enclose, surround, or encompass a defined region of space. Therefore, according to these defined terms, a continuous line which is traced around a region of space and which starts and ends at the same location "circumscribes" the region of space and has a "circumference" which is defined by the distance the line travels as it translates along the path circumscribing the space.

Still further, a circumferential path or element may include one or more of several shapes, and may be, for example, circular, oblong, ovular, elliptical, or otherwise planar enclosures. A circumferential path may also be three dimensional, such as, for example, two opposite-facing semi-circular paths in two different parallel or off-axis planes that are connected at their ends by line segments bridging between the planes.

Figure 1A:
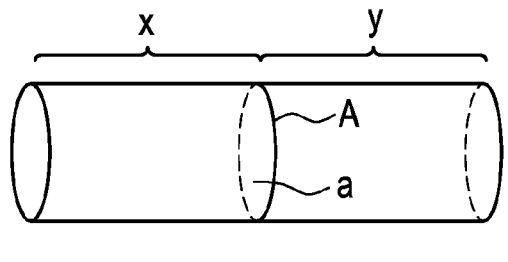
FIGS. 1A-F shows schematic views of different types of circumferential patterns according to the invention.
Figure 1B:
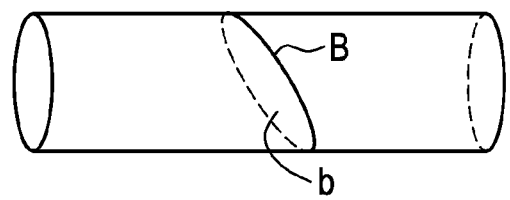
Figure 1C:
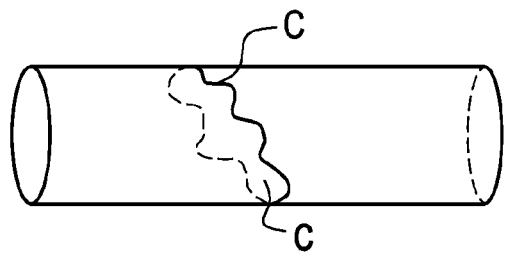
Figure 1D:
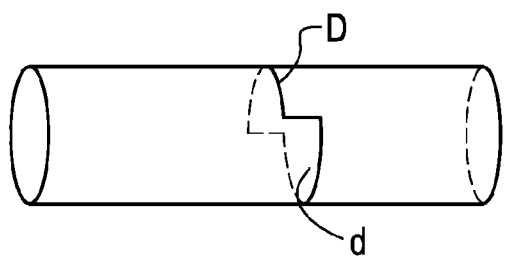

For purpose of further illustration, FIGS. 1A-E therefore show various circumferential paths A, B, C, D, and E respectively, each translating along a portion of a body space, such as a pulmonary vein wall, a vein ostium, or an atrial chamber, and circumscribing a defined region of space, shown at a, b, c, d, and e, also respectively, each circumscribed region of space being a portion of the body space or lumen. For still further illustration of the three-dimensional circumferential case shown in FIG. 1D, FIG. 1F shows an exploded perspective view of circumferential path D as it circumscribes multiplanar portions of the body lumen shown at d', d", and d''', which together make up region d as shown in FIG. 1D.

The term "transect", including derivatives thereof, is also herein intended to mean to divide or separate a region of space into isolated regions. For example, each of the regions circumscribed by the circumferential paths shown in FIGS. 1A-D transects the respective pulmonary vein or ostium, including its lumen and its wall, to the extent that the respective pulmonary vein is divided into a first longitudinal region located on one side of the transecting region, shown, for example, at region "x" in FIG. 1A, and a second longitudinal region on the other side of the transecting plane, shown, for example, at region "y" also in FIG. 1A.

Figure 1E:
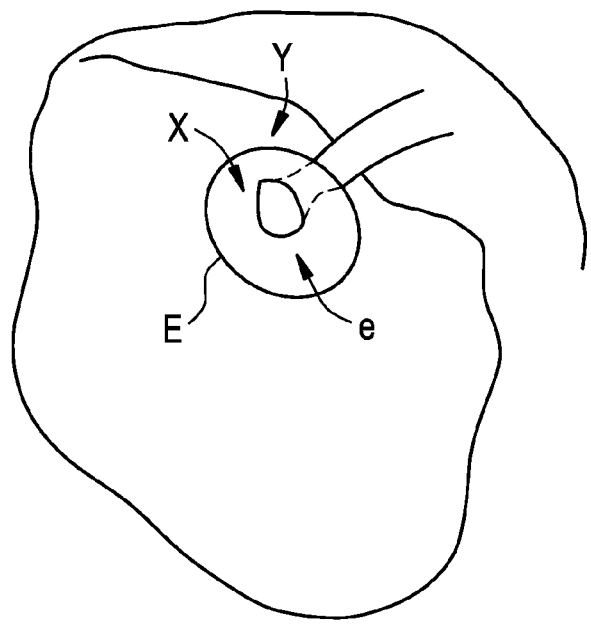
Figure 1F:
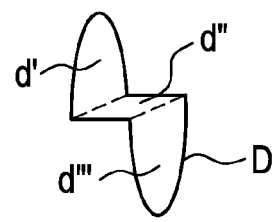

Similarly, the circumferential paths shown in FIG. 1E may transect a body space, such as a left atrium, such that the respective atrium is divided into first inner region located on the inside of the transecting region, shown for example as region "x" in FIG. 1E, and a second outer region on the other side of the transecting path, shown for example at region "y" also in FIG. 1E.

Therefore, a "circumferential conduction block" according to the present invention is formed along a region of tissue which follows a circumferential path, such as along the pulmonary vein wall, ostium or atrial chamber, and circumscribing and transecting the region of tissue relative to electrical conduction along its longitudinal axis. The transecting circumferential conduction block therefore isolates electrical conduction between opposite longitudinal portions of the region of tissue relative to the conduction block and along the longitudinal axis.

The terms "ablate" or "ablation," including derivatives thereof, are hereafter intended to mean the substantial altering of the mechanical, electrical, chemical, or other structural nature of tissue. In the context of intracardiac ablation applications shown and described with reference to the variations of the illustrative embodiment below, "ablation" is intended to mean sufficient altering of tissue properties to substantially block conduction of electrical signals from or through the ablated cardiac tissue.

The term "element" within the context of "ablation element", including derivatives thereof, is herein intended to mean a discrete element, such as an electrode, or a plurality of discrete elements, such as a plurality of spaced electrodes, which are positioned so as to collectively ablate a region of tissue.

Therefore, an "ablation element" according to the defined terms may include a variety of specific structures adapted to ablate a defined region of tissue. For example, one suitable ablation element for use in the present invention may be formed, according to the teachings of the embodiments below, from an "energy emitting" type element which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a radiofrequency ("RF") current source; an antenna element which is energized by a microwave energy source; a heating element, such as a metallic element or other thermal conductor which is energized to emit heat such as by convective or conductive heat transfer, by resistive heating due to current flow, or by optical heating with light; a light emitting element, such as a fiber optic element which transmits light sufficient to ablate tissue when coupled to a light source; a cryogenic ablation element (cryoablation) which cools the tissue sufficient to change the tissue's characteristics; an ultrasonic element such as an ultrasound crystal element which is adapted to emit ultrasonic sound waves sufficient to ablate tissue when coupled to a suitable excitation source; or an ionizing ablation elements that emits ionizing radiation sufficient to ablate tissue.

In addition, other elements for altering the nature of tissue may be suitable as "ablation elements" under the present invention when adapted according to the detailed description of the invention below. For example, a cryoablation element adapted to sufficiently cool tissue to substantially alter the structure thereof may be suitable if adapted according to the teachings of the current invention.

Furthermore, a fluid ablation element, such as a wall that is porous or has a discrete port (or a plurality of ports) is fluidly coupled to a fluid delivery source, may be adapted to couple an ablation medium to the tissue for ablation. In one aspect, the fluid ablation element may infuse the ablation medium, such as a fluid containing alcohol, directly into the tissue adjacent to the wall in order to substantially alter the nature of that tissue. In another aspect, the fluid ablation element may supply radiofrequency or other mode of electrical current to the tissue by electrically coupling an electrical ablation element to the tissue via an ablation medium which is an electrically conductive fluid, such as for example an ionic fluid which may be, in one illustrative variation, hypertonic saline. Moreover, the terms "ablation medium" are intended to mean a medium that cooperates with one or more of the assemblies herein described in order to directly couple to and ablate the intended tissue.

The terms "porous" or "permeable", including derivatives thereof, are herein used interchangeably and are intended to mean a material wall construction having sufficient void volume to allow a substance to permeate into and across the wall, including allowing for such substrate to elude through and out from the wall, such as by weeping or in fluid jets, or by merely "absorbing" the substrate into the void volume in the wall wherein substantial flow of the substrate completely through and from the wall is substantially limited or even prevented. Examples of "porous" or "permeable" materials for the purpose of illustration include without limitation: a material wall with inherent void volume upon formation of the wall; a material wall that is not inherently porous but with apertures formed therethrough such as for example by mechanical drilling or laser/optical drilling; and a material wall with chemically formed void volume.

Design of Particular Embodiments

One circumferential ablation element design that is believed to provide a highly useful embodiment of the present invention is shown in FIG. 2. As described in further detail below, this and other circumferential ablation element designs are believed to be particularly useful for tissue ablation along a region where a pulmonary vein extends from a left atrium, including areas along the atrial wall, in the treatment of atrial fibrillation, including ablating areas along the atrial wall. As shown in FIG. 2, the design includes a circumferential ablation member (200) with two insulators (202, 204) that encapsulate the proximal and distal ends, respectively, of the working length L of an expandable member (210). In the particular embodiment shown, the insulators (202,204) are distinct layers of material that cover a balloon skin (212) of balloon or expandable member (210). By providing these spaced insulators, a circumferential band (203) of uninsulated balloon skin is located between the opposite insulators.

The expandable member (210) as shown in FIG. 2 is joined at its proximal end to elongate body (201) that extends proximal to the expandable member (210). More particularly, FIG. 2 shows the expandable member (210) and the elongate body (201) as being integrally formed, with the elongate body (201) extending from the expandable member (210) to the proximal end of the device outside of the patient (not shown). The distal end of the expandable member (210) is mounted to inner member (221) that extends through the elongate body (201) and expandable member (210) to the proximal end of the device. A lumen within the inner member (221) allows passage of a guidewire, as described in further detail below. The lumen defined between the elongate body (201) and the inner member (221) provides a passageway for fluids used in ablation and/or inflation of balloon (210). It will be appreciated that other designs may also be used for the circumferential ablation member. For instance, the expandable member (210) need not be integral with the elongate body (201), and may be separately mounted.

It is further noted that this embodiment is not limited to a particular placement of the ablation element. Rather, a circumferential band may be formed anywhere along the working length of the expandable member and circumscribing the longitudinal axis of the expandable member as previously described.

The balloon construction shown in FIG. 2 forms an RF ablation electrode. An electrode (220) is provided on inner member (221) and is coupled to an ablation actuator shown at radiofrequency ("RF") current source (230) via electrical lead (225), thereby forming an internal current source within balloon (210). RF current source (230) is coupled to both the RF electrode element and also a ground patch (295) that is in skin contact with the patient to complete an RF ablation circuit. A porous membrane such as an expanded fluoropolymer, and more particularly an expanded polytetrafluoroethylene material, comprises the entire balloon skin (212) of expandable member (210). The porous skin (212) may be constructed according to several different methods, such as by forming holes in an otherwise contiguous polymeric material, including mechanically drilling or using laser energy, or the porous skin may simply be an inherently permeable material with inherent void volume forming pores for permeability, as will be developed according to more particular illustrative embodiments below. By insulating the proximal and distal end portions of the working length of the expandable member as shown in FIG. 2, only the pores along the circumferential band of the uninsulated intermediate region are allowed to ablatively couple the electrolyte which carries an ablative RF current into tissue. This uninsulated intermediate region thus forms a permeable section, while the insulated regions of the expandable member are non-permeable sections.

It will further be appreciated that in the illustrated embodiment where the balloon (210) is integral with the elongate body (201), the elongate body (201) is nonporous to prevent fluid from passing through the wall of the elongate body (201) before reaching the balloon chamber. In another embodiment, the insulator (202) may extend over the elongate body (201) to insulate the elongate body (201).

According to operation of the FIG. 2 assembly, an ablative fluid medium that is electrically conductive, such as for example a hypertonic saline solution, passes from a source (240) and into the internal chamber defined by the skin and outwardly into the porous wall of the balloon skin along the intermediate region until the solution directly couples to tissue. By electrically coupling the fluid within the porous balloon skin to an RF current source (230) via electrode (220), the porous region of the expandable member functions as an RF electrode wherein RF current flows outwardly into the tissue engaged by the balloon via the conductive fluid absorbed into the porous intermediate region of the wall.

The ablation actuator mechanism for the overall assembly, such as including current source (230), may also include or be coupled to a monitoring circuit (not shown) and/or a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

In addition, one further illustrative embodiment (not shown) which is also contemplated provides an outer skin with the selectively porous intermediate region externally of another, separate expandable member, such as a separate expandable balloon, wherein the conductive fluid coupled to a current source is contained in a region between the outer skin and the expandable member contained therein.

FIG. 2 broadly illustrates an ablation balloon construction wherein an ablative surface is provided along the entire working length of an expandable member, but the surface is shielded or insulated from releasing ablative energy into surrounding tissues except for along an unshielded or uninsulated equatorial band. As such, the insulator embodiment contemplates other ablation elements which are provided along the entire working length of an expandable member and which are insulated at their ends to selectively ablate tissue only about an uninsulated equatorial band. Other RF electrode arrangements are also considered suitable for use according to the selectively insulated ablation balloon embodiment shown in FIG. 2. In one further illustrative example, a metallized balloon includes a conductive balloon skin wherein the electrical insulators, such as polymeric coatings, are positioned over or under each end of the working length and thereby selectively ablate tissue with electricity flowing through the uninsulated equatorial band. The balloon skin may itself be metallized, such as by mixing conductive metal, including but not limited to gold, platinum, or silver, with a polymer to form a compounded, conductive matrix as the balloon skin. Or a discrete electrode element may be secured onto an outer surface of the balloon skin, such as in the embodiment when an expandable balloon is placed within an outer skin of selected porosity as just described above. In another example, the porous aspects of the circumferential band are beneficially applied in a chemical ablation element mode, wherein a chemically ablative fluid medium such as an alcohol based medium is absorbed within the wall of the circumferential band and coupled to the tissue engaged to the band for ablation.

In the alternative, or in addition to the RF electrode variations just described, the circumferential ablation member provided by the ablation balloon described may also include other ablative energy sources or sinks, and particularly may include a thermal conductor that circumscribes the outer circumference of the working length of an expandable member. Examples of suitable thermal conductor arrangements include a metallic element that may, for example, be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be, for example, a polymeric balloon skin that is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40 deg and 80 deg Celsius.

The various alternative ablation elements such as those just described may further incorporate the various other embodiments such as methods of manufacture or use, and fall within the present invention.

It is further contemplated that the insulators described may be only partial and still provide the relatively isolated ablative tissue coupling along the circumferential band. For instance, in the conductive RF electrode balloon case, a partial electrical insulator will allow a substantial component of current to flow through the uninsulated portion due to a "shorting" response to the lower resistance in that region. In another illustrative construction, balloon skin (212) may be thermally conductive to surrounding tissue when inflated with a heated fluid which may contain a radiopaque agent, saline fluid, ringers lactate, combinations thereof, or other known fluids having acceptable heat transfer properties for these purposes.

FIG. 2 further shows use of a electrode element (220) as a radiopaque marker to identify the location of the circumferential band (203) in order to facilitate placement of that band at a selected ablation region of a pulmonary vein via X-ray visualization. Electrode element (220) is opaque under X-ray, and may be constructed, for example, of a radiopaque metal such as gold, platinum, or tungsten, or may comprise a radiopaque polymer such as a metal loaded polymer. FIG. 2 shows electrode element (220) positioned coaxially over an inner tubular member (221) that is included in a coaxial catheter design as would be apparent to one of ordinary skill. The present invention contemplates the combination of such a radiopaque marker additionally in the other embodiments herein shown and described. To note, when the circumferential ablation member that forms an equatorial band includes a metallic electrode element, such electrode may itself be radiopaque and may not require use of a separate marker. Moreover, various contemplated designs do not require positioning of the electrode (220) exactly along the band region, and therefore such electrode may be replaced with a simple radiopaque marker in order to retain the ability to locate the band within the body via X-ray visualization.

The expandable member of the embodiments shown may take one of several different forms, although the expandable member is generally herein shown as an inflatable balloon that is coupled to an expansion actuator which is a pressurizeable fluid source. The expandable member forms a fluid chamber that communicates with a fluid passageway (not shown in all the figures) that extends proximally along the elongate catheter body and terminates proximally in a proximal fluid port that is adapted to couple to the pressurizeable fluid source.

The embodiment of FIG. 2 describes the expandable member (210) as being a balloon made of a porous fluoropolymer, such as an expanded polytetrafluoroethylene material It will be appreciated that various other materials may also be suitable for the balloon, or portions of the balloon, as described for the various embodiments herein. Several possible balloon materials are described below. These materials may have inherent porosity as would be known to one of skill in the art, or may be made porous according to several different methods, such as forming holes in an otherwise contiguous polymeric material.

In one expandable balloon variation, the balloon or portion thereof may be constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters, with each balloon working length having a unique predetermined expanded diameter, may be provided from which a treating physician may choose a particular device to meet a particular patient's pulmonary vein anatomy.

In an alternative expandable balloon variation, the balloon may be constructed of a relatively compliant, elastomeric material, such as, for example (but not limited to), a silicone, latex, polyurethane, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with higher pressure inflations, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

According to one elastomeric construction that is believed to be highly beneficial for engaging large pulmonary vein ostia, such as ranging from 1-2.5 centimeters in diameter, the balloon is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taught configuration. In other words, "expansion" is herein intended to relate to change in diameter that is attributable to the material compliance in a stress-strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position between about 0.060 to 0.200 inches, inclusive to a radially expanded position between about 0.25 and 1.5 inches, inclusive.

Moreover, a circumferential ablation member is adapted to conform to the geometry of the pulmonary vein ostium, at least in part by providing substantial compliance to the expandable member, as will be further developed below. Further to this conformability, such as is shown by reference to FIG. 5A, the working length L of expandable member (570) is also shown to include a taper which has a distally reducing outer diameter from a proximal end (571) to a distal end (573). In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Other expandable members than a balloon may also be suitable according to the insulator aspects of the invention. For example, various modes of known expandable cages may be sufficient expandable members for this invention so long as a fluid chamber is at least in part enclosed by or otherwise associated with the cage so as to provide for ablative fluid coupling to tissue as broadly contemplated by the disclosed embodiments.

It is to be appreciated that the circumferential band (203) shown in FIG. 2 and elsewhere throughout the figures generally has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band that has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

Further to the relatively narrow circumferential band aspect of the invention, the circumferential lesion formed may also be relatively narrow when compared to its own circumference, and may be less than two-thirds or even one-half its own circumference on the expandable element when expanded. In one arrangement that is believed to be suitable for ablating circumferential lesions in heart chambers or pulmonary veins, the band width w is less than 1 cm with a circumference on the working length when expanded that is greater than 1.5 cm.

Still further to the FIG. 2 embodiment, energy is coupled to the tissue largely via the ablative medium supplied by the inflation fluid and porous or permeable balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, several different balloon types may be provided for ablating different tissue structures so that a particular shape may be chosen for a particular region of tissue to be ablated, such as for example in order to accommodate differing geometries encountered when ablating circumferential regions of tissue to isolate various different pulmonary veins in either the same of different patients, as further developed elsewhere hereunder.

The elongate body (201) of the overall catheter assembly shown in FIG. 2, and as appropriate elsewhere throughout this disclosure, may have an outer diameter provided within the range of from about 5 French to about 10 French, and more preferable from about 7 French to about 9 French. In "guidewire tracking designs" as shown in FIG. 2, the guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although the diameter may vary based upon the viscosity of inflation medium used, length of the lumen, and other dynamic factors relating to fluid flow and pressure.

The elongate body (201) should also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion of the body (201) is preferably flexible and adapted to track over and along a guidewire seated within the targeted pulmonary vein. In one further more detailed construction that is believed to be suitable, the proximal end portion is adapted to be at least 30% stiffer than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the circumferential ablation member to the desired ablation region are also contemplated. For example, while the FIG. 2 variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation.

Further to this latter variation, the guidewire lumen and guidewire of the FIG. 2 variation may be replaced with a "pullwire" lumen and associated fixed pullwire that is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

Figure 3A:
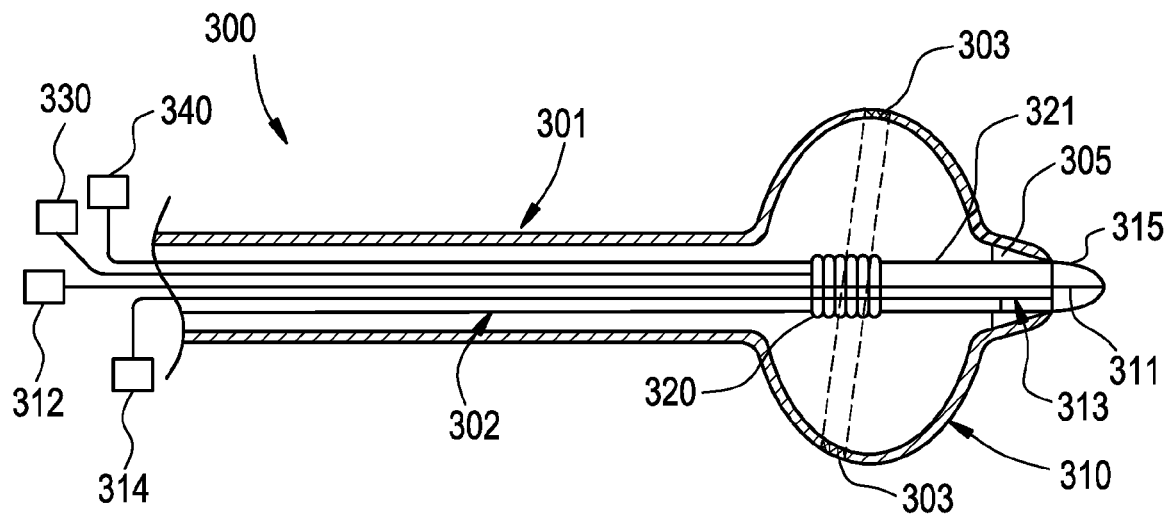
FIGS. 3A-B show longitudinal cross-sectional and perspective views, respectively, of another circumferential ablation device having a similar balloon ablation member as shown in FIG. 2, except showing the balloon ablation member secured to the distal end portion of a steerable delivery member.
Figure 3B:
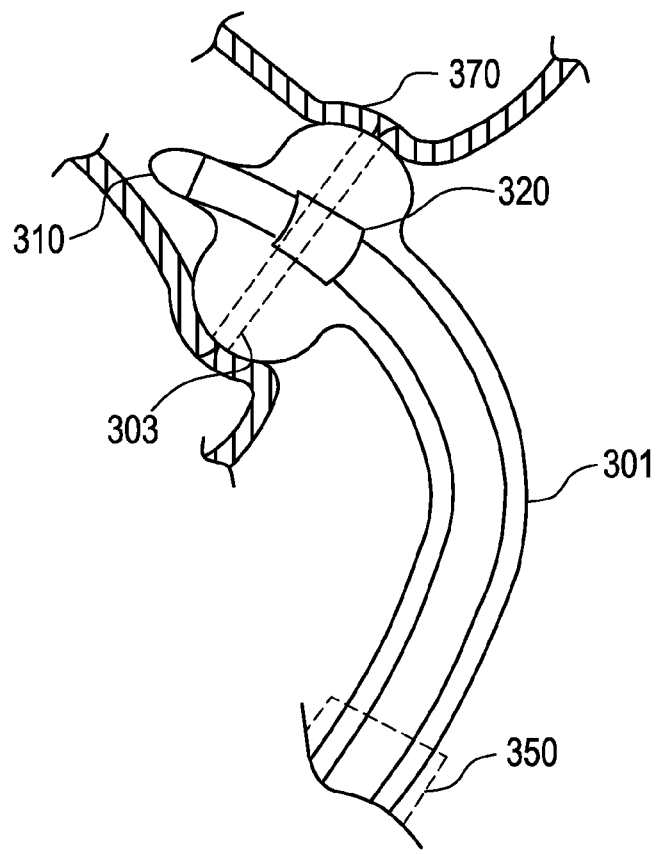

FIGS. 3A-B illustrate such an additional variation of the tissue ablation device assembly (300) wherein an ablation balloon (310) is beneficially secured over a steerable delivery member (302) which may be similar for example to deflectable tip electrode catheter and/or according to various steerable cardiac electrophysiology mapping catheters, such as those known in the art. Outer member (301) is shown coaxially disposed over steerable delivery member (302) such that permeable band (303) of balloon (310) provided by outer sheath (301) is disposed around electrode (320) provided on the steerable delivery member (302). Inflation device (340) is fluidly coupled with the inner fluid chamber formed by balloon (310) and includes a pressurized source of an ablative medium such as electrically conductive fluid. An ablation actuator, which in the FIG. 3A embodiment is RF current source (330), is coupled with electrode (320). Furthermore, tip electrode mapping/actuator assembly (314) is also shown coupled with tip electrode (315) via tip electrode lead (313). Further to the particular variation shown in FIGS. 3A-B, the distal end of pullwire (311) is schematically shown to be secured to the distal end of the steerable delivery member (301), whereas the proximal end of pullwire (311) is shown coupled to deflection actuator (312) which is adapted to controllably provide forces on pullwire (311) such that the distal end of assembly (300) is deflected or shaped as desired for torsional steering.

Balloon (310) is secured to the outer surface (321) of steerable delivery member (302) via bond (305) such that a fluid tight seal is provided and further such that balloon (310) and steerable delivery member (302) are in a fixed relationship to each other such that they may be manipulated and controllably positioned together via transcatheter techniques. A preferred mode for use of assembly 300 in FIG. 3A is shown in FIG. 3B. This figure illustrates assembly (300) delivered into a left atrium through a transeptal sheath (350), wherein it is shaped and positioned within a pulmonary vein. More specifically, band (303) is engaged to circumferential region of tissue (370) in order to ablatively couple electrode (320) through band (303) and to tissue (370) via the ablative fluid medium absorbed into the wall of band (303).

The electrode (320) need not be positioned exactly along band (303) relative to the long axis of device assembly (300) in order to electrically couple the electrode to fluid and thereby to the band and tissue surrounding the band. However, as electrode (320) is preferably a radiopaque material such as a metal, and considering an increase in impedance when moving electrode (320) further away from band (303), the embodiment shown is believed to be highly beneficial. If another electrical source were provided such that there were no electrode (320) within balloon (310), then a separate radiopaque band may be provided at a similar location where electrode (320) is shown in FIG. 3A in order to provide a marker to position band (303) where desired, such as along circumferential region of tissue (370) as shown in FIG. 3B.

Figure 4A:
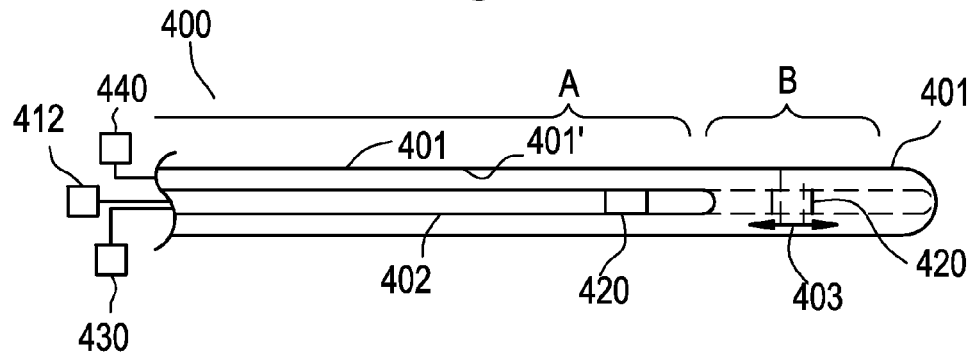
FIG. 4A-C show various views of a circumferential ablation device similar to that shown in FIGS. 3A-B, except showing the balloon ablation member disposed around a steerable delivery member such that the steerable delivery member is moveable within the balloon ablation member.
Figure 4B:
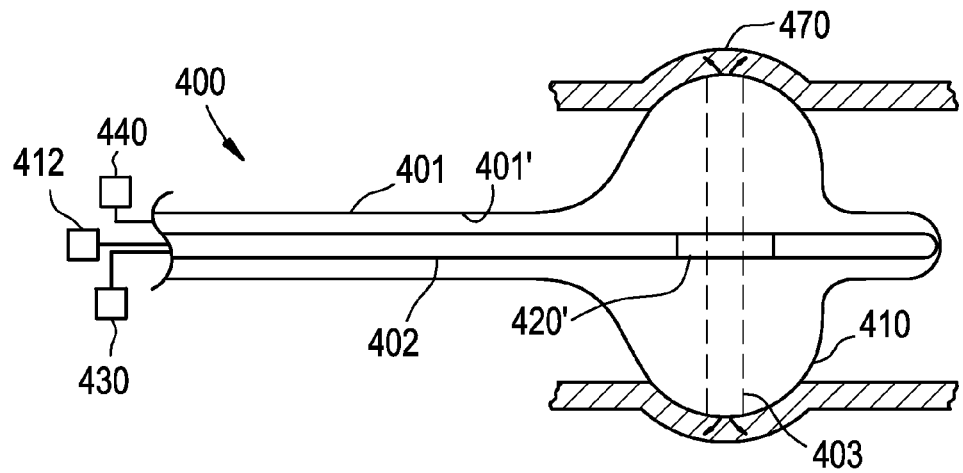
Figure 4C:
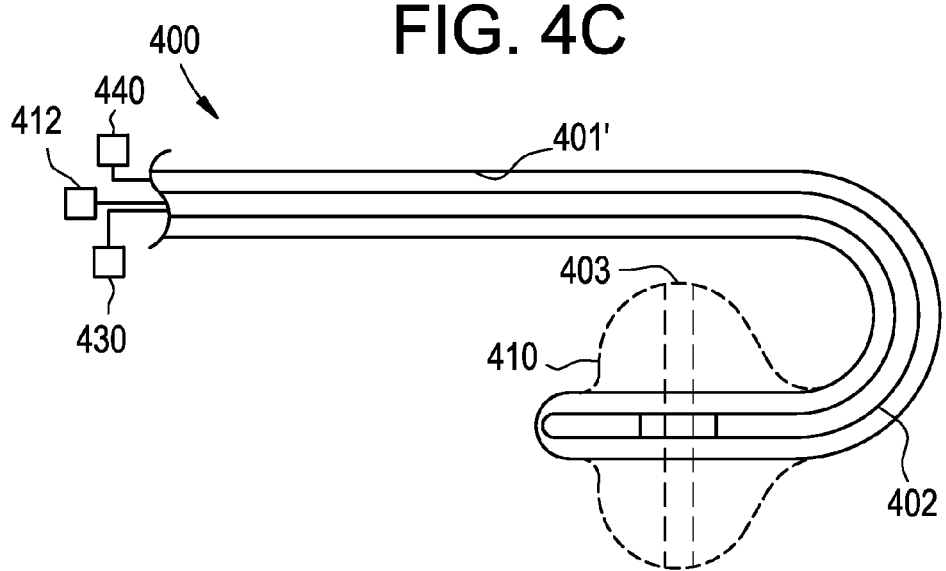

The FIG. 4A-C embodiment provides a steerable electrode catheter/balloon assembly (400) that differs from the FIG. 3A-C embodiment in that the steerable delivery member (402) in FIGS. 4A-C is moveably engaged within an interior passageway of a separate outer member (401) that provides balloon (410) in a separate sheath assembly that surrounds steerable delivery member (402). Section A in FIG. 4A indicates the portion of the outer member (401) that does not expand when filled with fluid, while Section B in FIG. 4B defines the balloon portion that does expand when filled with fluid. More specifically, outer member (401) is characterized as being: (a) closed at the distal end; and (b) inflatable along balloon (410) if pressurized with fluid from pressurizeable fluid source (440) containing electrically conductive fluid. By advancing the steerable delivery member (402) within passageway (401'), electrode (420) is aligned with band (403) such that expansion of balloon (410) and actuation of electrode (420) ablates a circumferential band of tissue (470) engaged to band (403), as shown in FIG. 4B. Moreover, as in FIGS. 3A-C, the steerable delivery member (402) is preferably of the deflectable variety known in the art, and therefore allows for controllable positioning of the balloon (410) before, during, or after expansion and circumferential ablation, wherein such deflection is shown for the purpose of illustration in FIG. 4C. Beneficially, however, this FIG. 4A-C embodiment allows for the outer member (401) to be selectively fit over and used with any commercially available steerable catheters, such as for example commercially available, "deflectable tip" RF ablation catheters.

In order to add the proper positioning of the electrode (420) within the balloon (410) relative to band (403), some form of indicia may be provided on either or both of outer and inner catheters of this assembly, such as either visible markings on portions of the associated members extending externally of the body, or radiopaque markers that allow x-ray guided alignment of the assemblies.

Figure 5A:
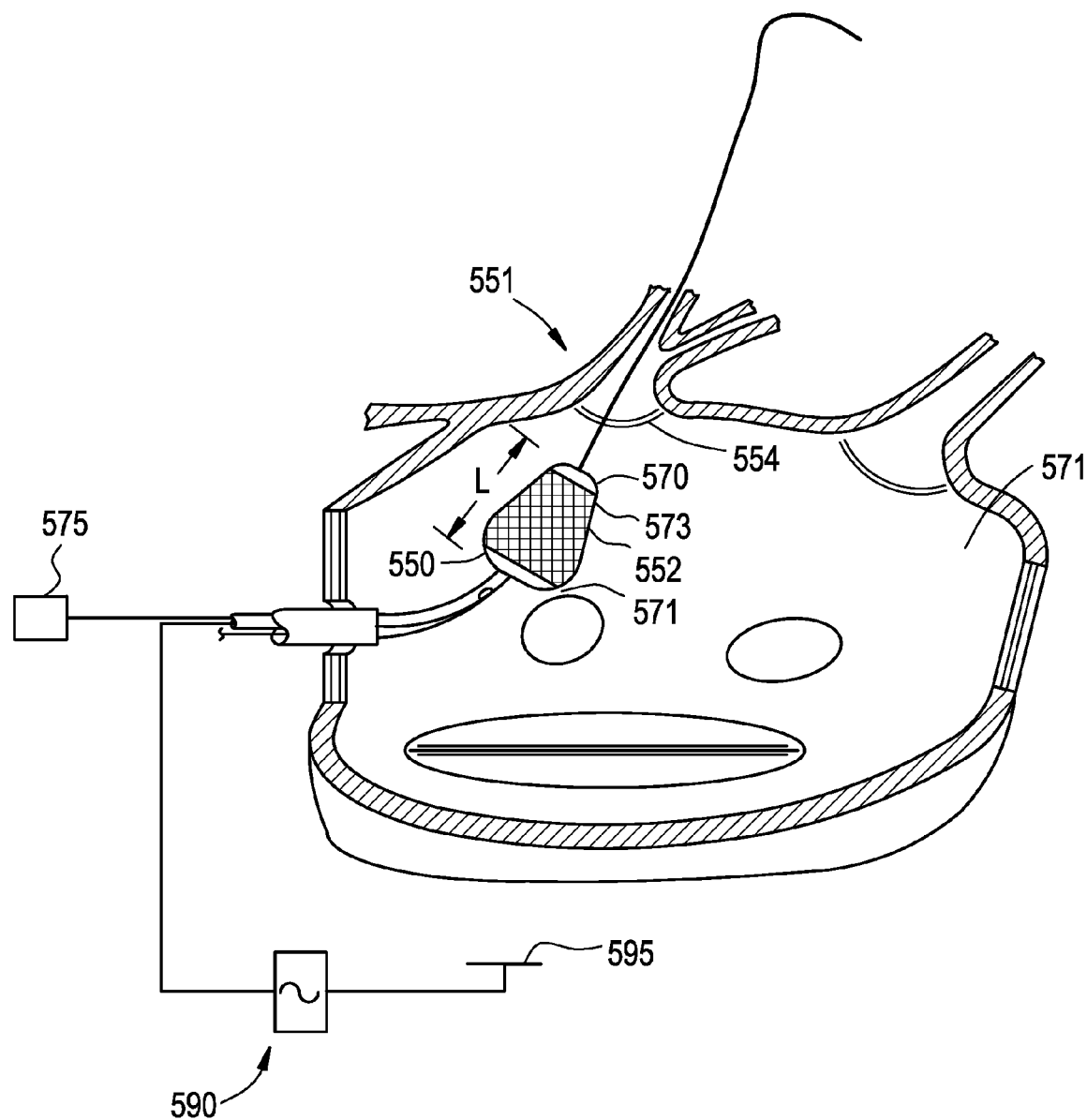
FIGS. 5A-B show various modes of using a circumferential ablation device to ablate a circumferential region of tissue along a location where a pulmonary vein extends from an atrium according to another mode of the invention.
Figure 5B:
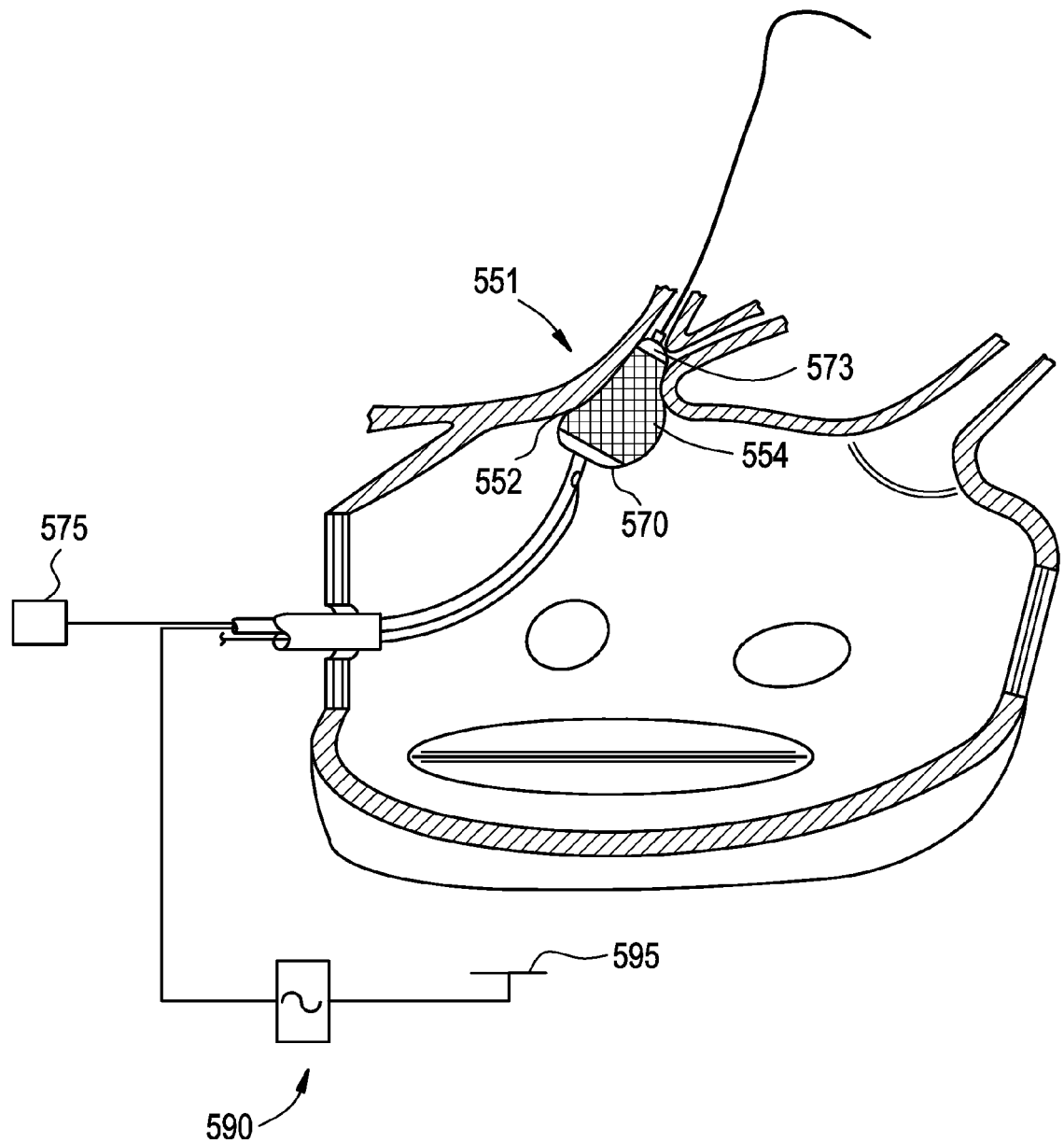
Figure 5C:
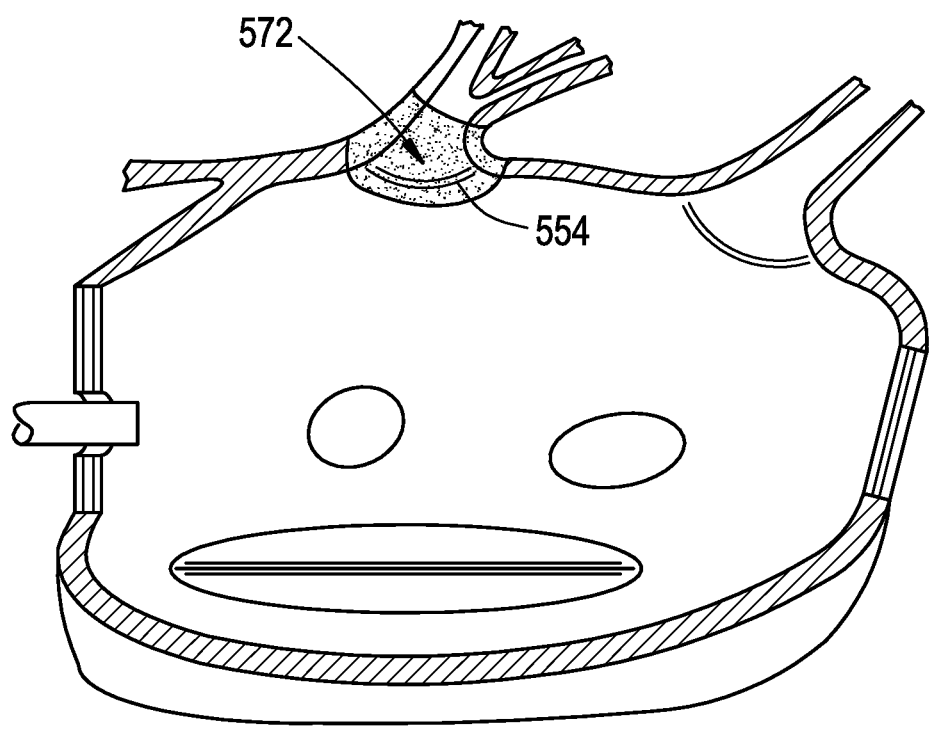
FIG. 5C shows a sectional view of a circumferential conduction block in a pulmonary vein as formed by a circumferential ablation device such as according to the modes shown in FIGS. 5A-B.

FIGS. 5A-B show a further variation in another embodiment of the present invention, wherein a circumferential ablation member (550) includes a radially compliant expandable member (570) which is adapted to conform to a pulmonary vein ostium (554) at least in part by adjusting it to a radially expanded position while in the left atrium and then advancing it into the ostium. FIG. 5A shows expandable member (570) after being adjusted to a radially expanded position while located in the left atrium (571). FIG. 5B further shows expandable member (570) after being advanced into the pulmonary vein (551) until at least a portion of the expanded working length L of circumferential ablation member (550), which includes a circumferential band (552), engages the pulmonary vein ostium (554). FIG. 5C shows a portion of a circumferential lesion (572) that forms a circumferential conduction block in the region of the pulmonary vein ostium (554) subsequent to actuating the circumferential ablation element to form the circumferential lesion.

In addition to conforming to the pulmonary vein ostium, expandable member (570) is also shown in FIG. 5B to engage a circumferential path of tissue along the left posterior atrial wall which surrounds ostium (554). Moreover, circumferential band (552) of the circumferential ablation member is also thereby adapted to engage that atrial wall tissue. Therefore, the circumferential conduction block formed according to the method shown and just described in sequential steps by reference to FIGS. 5A-B, as shown in-part in FIG. 5C, includes ablating the circumferential path of atrial wall tissue which surrounds ostium (554). Accordingly, the entire pulmonary vein, including the ostium, is thereby electrically isolated from at least a substantial portion of the left atrial wall which includes the other of the pulmonary vein ostia, as would be apparent to one of ordinary skill according to the sequential method steps shown in FIGS. 5A-B and by further reference to the resulting circumferential lesion (572) shown in FIG. 5C.

The lesion shown in FIG. 5C isolates the pulmonary vein, but is formed by ablating tissue surrounding the pulmonary vein, although while also within the pulmonary vein. It is further contemplated that such lesion may be formed only along the posterior left atrial wall and surrounding the pulmonary vein ostium, without also ablating tissue along the lumen or lining of the pulmonary vein or ostium, depending upon the particular shape of the balloon and/or position and geometry of the ablative band along that balloon. In one aspect of this embodiment, the compliant nature of the expandable member may be self-conforming to the region of the ostium such that the circumferential band is placed against this atrial wall tissue merely by way of conformability.

According to a further example, a pear-shaped balloon with a distally reducing outer diameter may provide a "forward-looking" face that, with the ablative band provided along that forward-looking face, is adapted to advance against such atrial wall tissue and ablate there. Such a pear shape may be preformed into the expandable member or balloon, or the member may be adapted to form this shape by way of controlled compliance as it expands, such as for example by the use of composite structures within the balloon construction. In any case, according to the "pear"-shaped variation, the circumferential band of the ablation member is preferably placed along the surface of the contoured taper which is adapted to face the left posterior atrial wall during use, such as for example according to the method illustrated by FIGS. 5A-B.

Figure 6A:
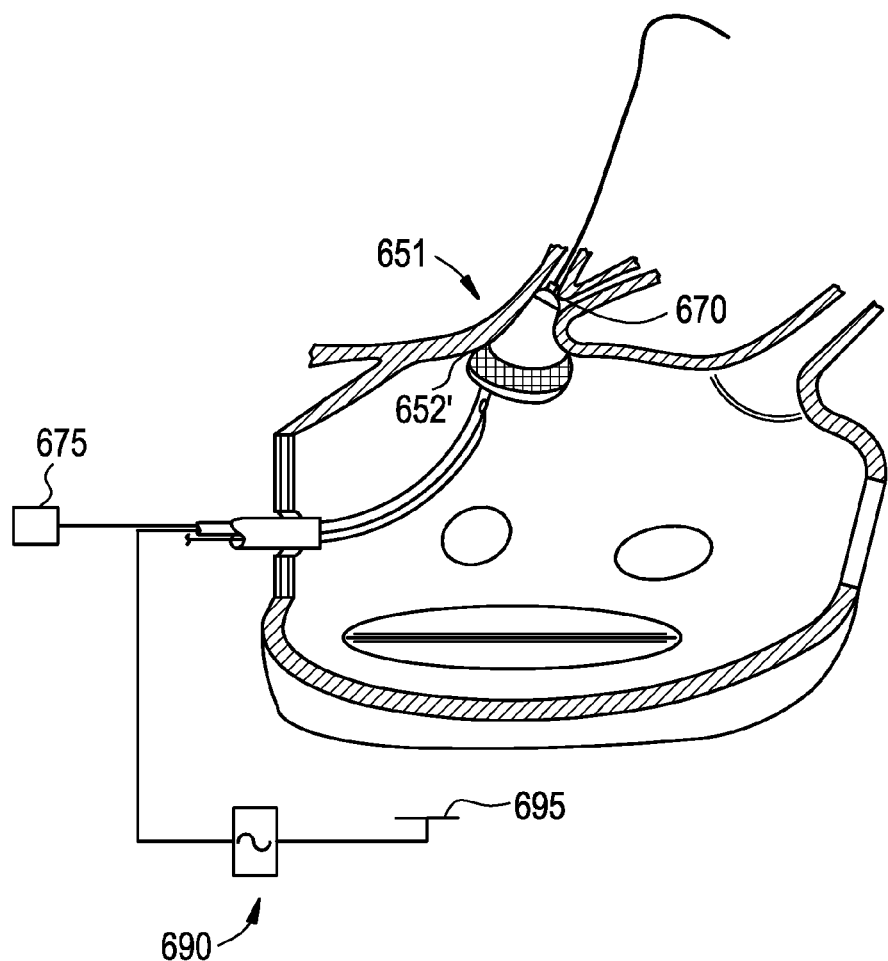
FIG. 6A shows one mode of using another circumferential ablation device according to the present invention in order to ablate a circumferential region of tissue along an atrial wall and surrounding a pulmonary vein ostium.
Figure 6B:
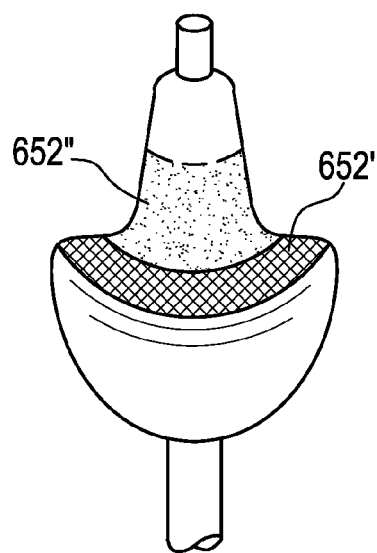
FIG. 6B shows a perspective view of a circumferential ablation member shows a "pear"-shaped balloon with an ablative circumferential band located at least in part along a "distal-looking" face along a contoured taper of the balloon.
Figure 6C:
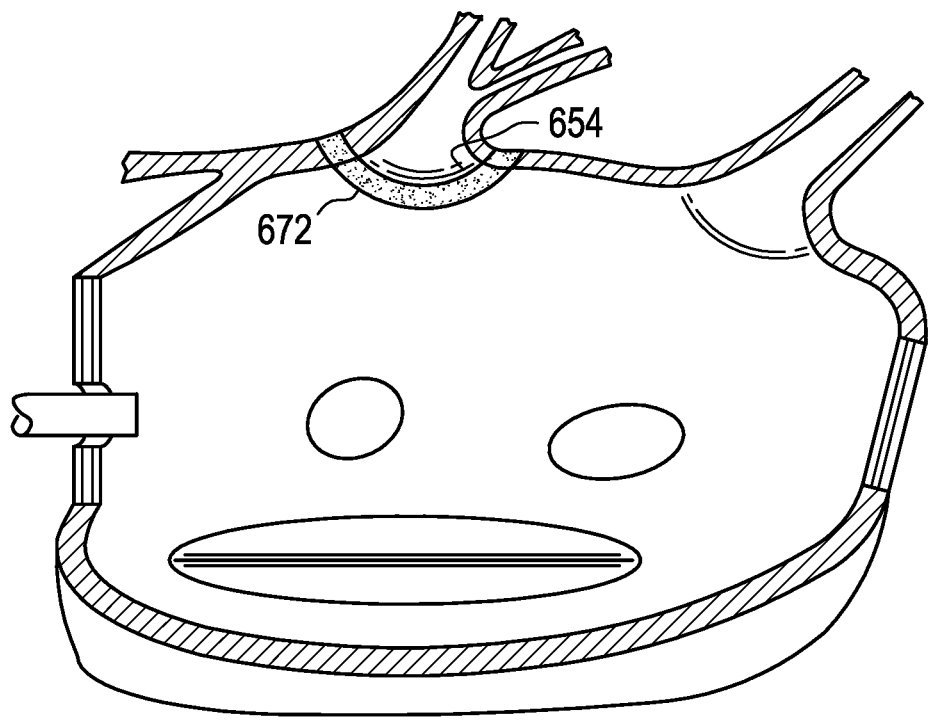
FIG. 6C shows a sectioned perspective view of a circumferential conduction block formed along the posterior left atrial wall and surrounding the pulmonary vein ostium.

FIGS. 6A-C show such a pear-shaped ablation balloon in a circumferential ablation member assembly adapted to electrically isolate a pulmonary vein and ostium from a substantial portion of the left posterior atrial wall. This embodiment isolates the pulmonary vein without also ablating tissue along the lumen or lining of the pulmonary vein or ostium.

In more detail, FIG. 6A shows circumferential band (652') to have a geometry (primarily width) and position along expandable member (670') such that it is adapted to engage only a circumferential path of tissue along the left posterior atrial wall which surrounds the pulmonary vein ostium. In one aspect of this embodiment, the compliant nature of the expandable member may be self-conforming to the region of the ostium such that the circumferential band is placed against this atrial wall tissue merely by way of conformability.

In another variation, a "pear"-shaped expandable member or balloon that includes a contoured taper may be suitable for use according to the FIG. 6A embodiment, as is shown by way of example in FIG. 6B. Such a pear shape may be preformed into the expandable member or balloon, or the member may be adapted to form this shape by way of controlled compliance as it expands, such as for example by the use of composite structures within the balloon construction. In any case, according to the "pear"-shaped variation, the circumferential band (652') of the ablation member is preferably placed along the surface of the contoured taper which is adapted to face the left posterior atrial wall during use according to the method illustrated by FIG. 6A. It is further contemplated that the ablation element may be further extended or alternatively positioned along other portions of the taper, such as is shown by example in shadow at extended band (652") in FIG. 6B. Accordingly, the variation shown in FIG. 6B to include extended band (652") may also adapt this particular device embodiment for use in forming circumferential conduction blocks also along tissue within the pulmonary vein and ostium, such as according to the previously described method shown in FIGS. 6A-C.

The tissue ablation device systems shown and described below are also believed to be beneficial for ablating tissue at certain locations where one or more pulmonary veins extend from an atrium.

Figure 7A:
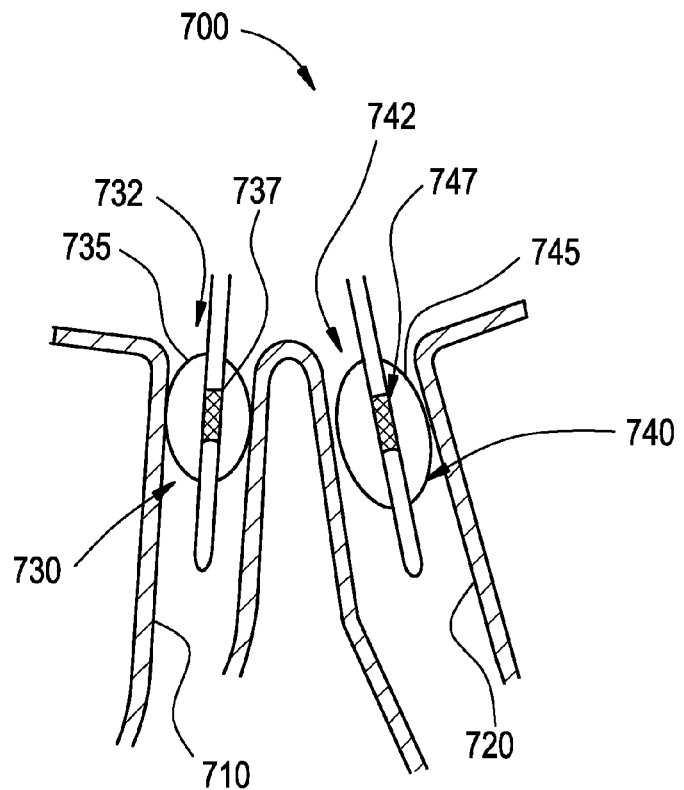
FIGS. 7A-B show sequential modes of use of a dual-ablation balloon system for ablating two circumferential regions of tissue at two locations, respectively, where two adjacent pulmonary vein branches, also respectively, extend from an atrial wall.
Figure 7B:
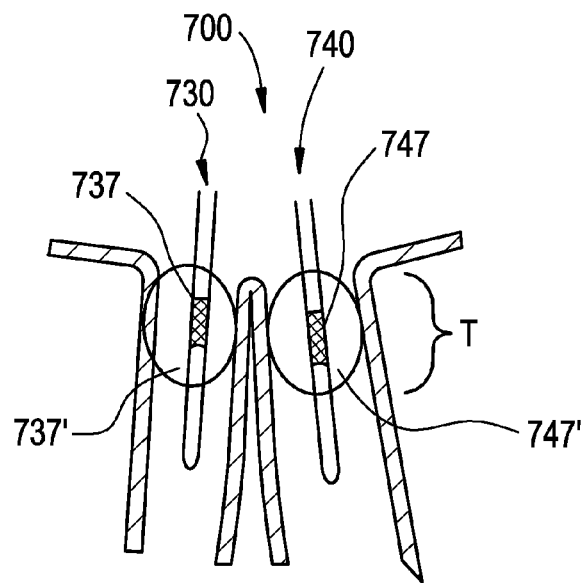

The tissue ablation device system (700) shown in FIGS. 7A-B includes two circumferential ablation devices (730, 740) in two pulmonary vein branches (710,720) which form adjacent ostia along an atrial wall. Each of devices (730,740) has a circumferential ablation member (732,742), respectively, which is shown to include an expandable member (735,745), also respectively, and an ablative energy source (737,747), also respectively. Each respective ablative energy source (737,747) is adapted to ablatively couple to a circumferential region of tissue at the base of the respective pulmonary vein (710,720), and if properly positioned, may combine to ablate tissue between the adjacent veins (710,720), as shown specifically in FIG. 7B wherein the expandable members expand the veins (710,720) to bring them together to assist the combined ablative coupling from each device to the tissue there between.

As earlier described the ablation element may also include an ultrasonic transducer. FIGS. 8A-8B show various specific embodiments of a circumferential ablation device assembly that utilizes an ultrasonic energy source to ablate tissue. The present circumferential ablation device has particular utility in connection with forming a circumferential lesion within or about a pulmonary vein ostium or within the vein itself in order to form a circumferential conductive block. This application of the present ablation device, however, is merely exemplary, and it is understood that those skilled in the art can readily adapt the present ablation device for applications in other body spaces.

As common to each of the following embodiments, a source of acoustic energy is provided to a delivery device that also includes an anchoring mechanism. In one mode, the anchoring device comprises an expandable member that also positions the acoustic energy source within the body; however, other anchoring and positioning devices may also be used, such as, for example, a basket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of about 1 to 10 mm. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIG. 8A through 8D, a circumferential ablation device assembly (800) includes an elongate catheter body (802) with proximal and distal end portions (810,812), an expandable balloon (820) located along the distal end portion (812) of elongate catheter body (802), and a circumferential ultrasound transducer (830) which forms a circumferential ablation member that is acoustically coupled to the expandable balloon (820). In more detail, FIGS. 8A-C variously show elongate catheter body (802) to include guidewire lumen (804), inflation lumen (806), and electrical lead lumen (808). The ablation device, however, can be of a self-steering type rather than an over-the-wire type device.

Each lumen extends between a proximal port (not shown) and a respective distal port, which distal ports are shown as distal guidewire port (805) for guidewire lumen (804), distal inflation port (807) for inflation lumen (806), and distal lead port (809) for electrical lead lumen (808). Although the guidewire, inflation and electrical lead lumens are generally arranged in a side-by-side relationship, the elongate catheter body (802) can be constructed with one or more of these lumens arranged in a coaxial relationship, or in any of a wide variety of configurations that will be readily apparent to one of ordinary skill in the art.

In addition, the elongate catheter body (802) is also shown in FIGS. 8A and 8C to include an inner member (803) that extends distally beyond distal inflation and lead ports (807, 809), through an interior chamber formed by the expandable balloon (820), and distally beyond expandable balloon (820) where the elongate catheter body terminates in a distal tip. The inner member (803) forms the distal region for the guidewire lumen (804) beyond the inflation and lead ports, and also provides a support member for the cylindrical ultrasound transducer (830) and for the distal neck of the expansion balloon, as described in more detail below.

One more detailed construction for the components of the elongate catheter body (802) that is believed to be suitable for use in transeptal left atrial ablation procedures is as follows. The elongate catheter body (802) itself may have an outer diameter provided within the range of from about 5 French to about 10 French, and more preferable from about 7 French to about 9 French. The guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although may vary based upon the viscosity of inflation medium used, length of the lumen, and other dynamic factors relating to fluid flow and pressure.

In addition to providing the requisite lumens and support members for the ultrasound transducer assembly, the elongate catheter body (802) of the present embodiment must also be adapted to be introduced into the left atrium such that the distal end portion with balloon and transducer may be placed within the pulmonary vein ostium in a percutaneous translumenal procedure, and even more preferably in a transeptal procedure. Therefore, the distal end portion (812) is preferably flexible and adapted to track over and along a guidewire seated within the targeted pulmonary vein. In one further more detailed construction that is believed to be suitable, the proximal end portion is adapted to be at least 30% stiffer than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the ultrasound ablation member to the desired ablation region are also contemplated. For example, while the FIG. 8A variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation. Further to this latter variation, the guidewire lumen and guidewire of the FIG. 8A variation may be replaced with a "pullwire" lumen and associated fixed pullwire which is adapted to deflect the catheter tip by applying tension along varied stiffness transitions along the catheter's length. Still further to this pullwire variation, acceptable pullwires may have a diameter within the range from about 0.008 inch to about 0.020 inch, and may further include a taper, such as, for example, a tapered outer diameter from about 0.020 inch to about 0.008 inch.

More specifically regarding expandable balloon (820) as shown in varied detail between FIGS. 8A and 8C, a central region (822) is generally coaxially disposed over the inner member (803) and is bordered at its end neck regions by proximal and distal adaptions (824,826). The proximal adaption (824) is sealed over elongate catheter body (802) proximally of the distal inflation and the electrical lead ports (807, 809), and the distal adaption (826) is sealed over inner member (803). According to this arrangement, a fluid tight interior chamber is formed within expandable balloon (820). This interior chamber is fluidly coupled to a pressurizeable fluid source (not shown) via inflation lumen (806). In addition to the inflation lumen (806), electrical lead lumen (808) also communicates with the interior chamber of expandable balloon (820) so that the ultrasound transducer (830), which is positioned within that chamber and over the inner member (803), may be electrically coupled to an ultrasound drive source or actuator, as will be provided in more detail below.

As earlier described, the expandable balloon (820) may be constructed from a variety of known materials, although the balloon (820) preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, but without limitation, Silicone, latex, or low durometer polyurethane (for example, a durometer of about 80 A).

In addition or in the alternative to constructing the balloon of highly compliant material, the balloon (820) can be formed to have a predefined fully inflated shape (i.e., be preshaped) to generally match the anatomic shape of the body lumen in which the balloon is inflated. For instance, as described earlier, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives, which may be acceptable as just described, the balloon (820) is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taut configuration. In other words, "expansion" is herein intended to relate to change in diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 mm to a radially expanded position of about 2.5 cm (or approximately 500% expansion ratio).

The ablation member illustrated in FIGS. 8A-D, takes the form of annular ultrasonic transducer (830). In the illustrated embodiment, the annular ultrasonic transducer (830) has a unitary cylindrical shape with a hollow interior (i.e., is tubular shaped); however, the transducer (830) can have a generally annular shape and be formed of a plurality of segments. For instance, the transducer (830) can be formed by a plurality of tube sectors that together form an annular shape. The tube sectors can also be of sufficient arc lengths so as when joined together, the sector assembly forms a "clover-leaf" shape. This shape is believed to provide overlap in heated regions between adjacent elements. The generally annular shape can also be formed by a plurality of planar transducer segments that are arranged in a polygon shape (e.g., hexagon). In addition, although in the illustrated embodiment the ultrasonic transducer comprises a single transducer element, the transducer can be formed of a multi-element array, as described in greater detail below.

As is shown in detail in FIG. 8D, cylindrical ultrasound transducer (830) includes a tubular wall (831) with three concentric tubular layers. The central layer (832) is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members (833,834) enclose central layer (832) within their coaxial space and are constructed of an electrically conductive material. In the illustrated embodiment, these transducer electrodes (833,834) comprise a metallic coating, and more preferably a coating of nickel, copper, silver, gold, platinum, or alloys of these metals.

One more detailed construction for a cylindrical ultrasound transducer for use in the present application is as follows. The length of the transducer (830) or transducer assembly (e.g., multi-element array of transducer elements) desirably is selected for a given clinical application. In connection with forming circumferential conduction blocks in cardiac or pulmonary vein wall tissue, the transducer length can fall within the range of approximately 2 mm up to greater than 10 mm, and preferably equals about 5 to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transeptally), for proper placement and location within a particular body space, and for achieving a desired ablation effect. In the given application within or proximate of the pulmonary vein ostium, the transducer (830) preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up to about 2 cm outer diameter of the balloon. For applications in other body spaces, the transducer applicator (830) may have an outer diameter within the range of about 1 mm to greater than 3-4 mm (e.g., as large as 1 to 2 cm for applications in some body spaces).

The central layer (832) of the transducer (830) has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer (830) in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer (830) is vibrated across the wall thickness and to radiate collimated acoustic energy in the radial direction. For this purpose, as best seen in FIGS. 8A and 8D, the distal ends of electrical leads (836,837) are electrically coupled to outer and inner tubular members or electrodes (833,834), respectively, of the transducer (830), such as, for example, by soldering the leads to the metallic coatings or by resistance welding. In the illustrated embodiment, the electrical leads are 4-8 mil (0.004 to 0.008 inch diameter) silver wire or the like.

The proximal ends of these leads are adapted to couple to an ultrasonic driver or actuator (840), which is schematically illustrated in FIG. 8D. FIGS. 8A-D further show leads (836, 837) as separate wires within electrical lead lumen (808), in which configuration the leads must be well insulated when in close contact. Other configurations for leads (836,837) are therefore contemplated. For example, a coaxial cable may provide one cable for both leads that is well insulated as to inductance interference. Or, the leads may be communicated toward the distal end portion 812 of the elongate catheter body through different lumens that are separated by the catheter body.

The transducer also can be sectored by scoring or notching the outer transducer electrode (833) and part of the central layer (832) along lines parallel to the longitudinal axis L of the transducer (830), as illustrated in FIG. 8E. A separate electrical lead connects to each sector in order to couple the sector to a dedicated power control that individually excites the corresponding transducer sector. By controlling the driving power and operating frequency to each individual sector, the ultrasonic driver (840) can enhance the uniformity of the ultrasonic beam around the transducer (830), as well as can vary the degree of heating (i.e., lesion control) in the angular dimension.

The ultrasound transducer just described is combined with the overall device assembly according to the present embodiment as follows. In assembly, the transducer (830) desirably is "air-backed" to produce more energy and to enhance energy distribution uniformity, as known in the art. In other words, the inner member (803) does not contact an appreciable amount of the inner surface of transducer inner tubular member (834). This is because the piezoelectric crystal which forms central layer (832) of ultrasound transducer (830) is adapted to radially contract and expand (or radially "vibrate") when an alternating current is applied from a current source and across the outer and inner tubular electrodes (833,834) of the crystal via the electrical leads (836,837). This controlled vibration emits the ultrasonic energy that is adapted to ablate tissue and form a circumferential conduction block according to the present embodiment. Therefore, it is believed that appreciable levels of contact along the surface of the crystal may provide a dampening effect that would diminish the vibration of the crystal and thus limit the efficiency of ultrasound transmission.

For this purpose, the transducer (830) seats coaxial about the inner member (803) and is supported about the inner member (803) in a manner providing a gap between the inner member (803) and the transducer inner tubular member (834). That is, the inner tubular member (834) forms an interior bore (835) that loosely receives the inner member (803). Any of a variety of structures can be used to support the transducer (830) about the inner member (803). For instance, spacers or splines can be used to coaxially position the transducer (830) about the inner member (803) while leaving a generally annular space between these components. In the alternative, other conventional and known approaches to support the transducer can also be used. For instance, O-rings that circumscribe the inner member (803) and lie between the inner member (803) and the transducer (830) can support the transducer (830) in a manner similar to that illustrated in U.S. Pat. No. 5,606,974 to Castellano issued Mar. 4, 1997, and entitled "Catheter Having Ultrasonic Device." More detailed examples of the alternative transducer support structures just described are disclosed in U.S. Pat. No. 5,620,479 to Diederich, issued Apr. 15, 1997, and entitled "Method and Apparatus for Thermal Therapy of Tumors." The disclosures of these references are herein incorporated in their entirety by reference thereto.

In the illustrated embodiment, at least one stand-off region (838) is provided along inner member (803) in order to ensure that the transducer (830) has a radial separation from the inner member (803) to form a gap filled with air and/or other fluid. In one preferred mode shown in FIG. 8C, stand-off region (838) is a tubular member with a plurality of circumferentially spaced outer splines (839) that hold the majority of the transducer inner surface away from the surface of the stand-off between the splines, thereby minimizing dampening affects from the coupling of the transducer to the catheter. The tubular member that forms a stand-off such as stand-off region (838) in the FIG. 8C embodiment may also provide its inner bore as the guidewire lumen in the region of the ultrasound transducer, in the alternative to providing a separate stand-off coaxially over another tubular member which forms the inner member, such as according to the FIG. 8C embodiment.

In a further mode, the elongate catheter body (802) can also include additional lumens which lie either side by side to or coaxial with the guidewire lumen (804) and which terminate at ports located within the space between the inner member (803) and the transducer (830). A cooling medium can circulate through space defined by the stand-off (838) between the inner member (803) and the transducer (830) via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer (830) desirably is electrically and mechanically isolated from the interior of the balloon (820). Again, any of a variety of coatings, sheaths, sealants, tubing and the like may be suitable for this purpose, such as those described in U.S. Pat. No. 5,620,479 to Diederich and U.S. Pat. No. 5,606,974 to Castellano. In the illustrated embodiment, as best illustrated in FIG. 8C, a conventional, flexible, acoustically compatible, and medical grade epoxy (842) is applied over the transducer (830). The epoxy (842) may be, for example, Epotek 301, Epotek 310, which is available commercially from Epoxy Technology, or Tracon FDA-8. In addition, a conventional sealant, such as, for example, General Electric Silicon II gasket glue and sealant, desirably is applied at the proximal and distal ends of the transducer (830) around the exposed portions of the inner member (803), wires (836, 837) and stand-off region (838) to seal the space between the transducer (830) and the inner member (803) at these locations.

An ultra thin-walled polyester heat shrink tubing (844) or the like then seals the epoxy coated transducer. Alternatively, the epoxy covered transducer (830), inner member (803) along stand-off region (838) can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer (830). As the tube shrinks, excess epoxy flows out and a thin layer of epoxy remains between the transducer and the heat shrink tubing (844). These layers (842,844) protect the transducer surface, help acoustically match the transducer (830) to the load, makes the ablation device more robust, and ensures air-tight integrity of the air backing.

Although not illustrated in FIG. 8A in order to simplify the drawing, the tubing (844) extends beyond the ends of transducer (830) and surrounds a portion of the inner member (803) on either side of the transducer (830). A filler (not shown) can also be used to support the ends of the tubing (844). Suitable fillers include flexible materials such as, for example, but without limitation, epoxy, Teflon® tape and the like.

The ultrasonic actuator (840) generates alternating current to power the transducer (830). The ultrasonic actuator (840) drives the transducer (830) at frequencies within the range of about 5 MHz to about 20 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator (840) can drive the transducer at frequencies within the range of 6.8 MHz and 7.2 MHz by continuously or discretely sweeping between these frequencies.

The ultrasound transducer (830) of the present embodiment sonically couples with the outer skin of the balloon (820) in a manner that forms a circumferential conduction block at a location where a pulmonary vein extends from an atrium as follows. Initially, the ultrasound transducer is believed to emit its energy in a circumferential pattern that is highly collimated along the transducer's length relative to its longitudinal axis L. The circumferential band therefore maintains its width and circumferential pattern over an appreciable range of diameters away from the source at the transducer. Also, the balloon is preferably inflated with fluid that is relatively ultrasonically transparent, such as, for example, degassed water. Therefore, by actuating the transducer (830) while the balloon (820) is inflated, the circumferential band of energy is allowed to translate through the inflation fluid and ultimately sonically couple with a circumferential band of balloon skin that circumscribes the balloon (820). Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

In one particular balloon-transducer combination shown in FIG. 8A, the ultrasound transducer preferably has a length such that the ultrasonically coupled band of the balloon skin, having a similar length d according to the collimated ultrasound signal, is shorter than the working length D of the balloon. According to this aspect of the relationship, the transducer is adapted as a circumferential ablation member that is coupled to the balloon to form an ablation element along a circumferential band of the balloon, therefore forming a circumferential ablation element band that circumscribes the balloon. Preferably, the transducer has a length that is less than two-thirds the working length of the balloon, and more preferably is less than one-half the working length of the balloon. By sizing the ultrasonic transducer length d smaller than the working length D of the balloon (820)—and hence shorter than a longitudinal length of the engagement area between the balloon (820) and the wall of the body space (e.g., pulmonary vein ostium)—and by generally centering the transducer (830) within the balloon's working length D, the transducer (830) operates in a field isolated from the blood pool. A generally equatorial position of the transducer (830) relative to the ends of the balloon's working length also assists in the isolation of the transducer (830) from the blood pool. It is believed that the transducer placement according to this arrangement may be preventative of thrombus formation that might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate catheter body (802) may include an additional radiopaque marker or markers (not shown) to identify the location of the ultrasonic transducer (830) in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The radiopaque marker is positioned coaxially over an inner tubular member (803).

The present circumferential ablation device is introduced into a pulmonary vein of the left atrium. Once properly positioned within the pulmonary vein or vein ostium, the pressurized fluid source inflates the balloon (820) to engage the lumenal surface of the pulmonary vein ostium. Once properly positioned, the ultrasonic driver (840) is energized to drive the transducer (830). It is believed that by driving the ultrasonic transducer (830) at 20 acoustical watts at an operating frequency of 7 MHz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

Figure 9A:
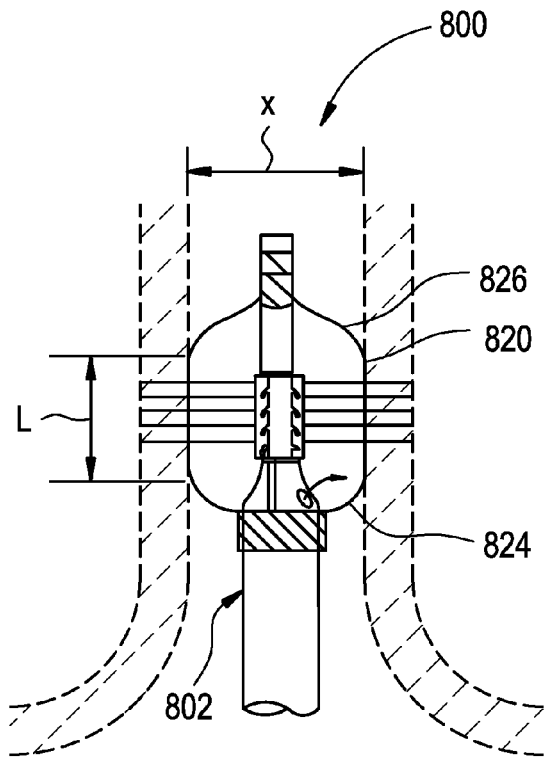
FIG. 9A shows a perspective view of a similar circumferential ablation catheter to the catheter shown in FIG. 8A, and shows the distal end portion of the circumferential ablation catheter during one mode of use in forming a circumferential conduction block at a location where a pulmonary vein extends from an atrium in the region of its ostium along a left atrial wall (shown in cross-section in shadow).
Figure 9B:
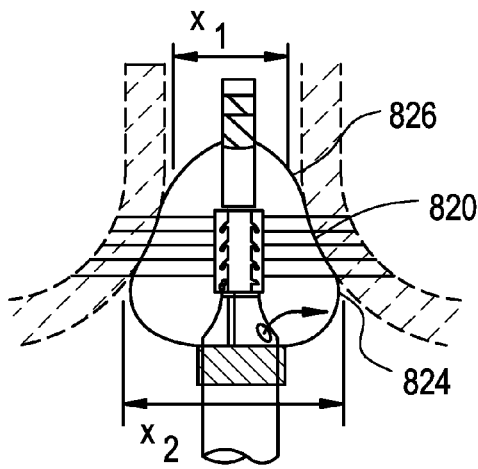
FIG. 9B shows a similar perspective and cross-section shadow view of a circumferential ablation catheter and pulmonary vein ostium as that shown in FIG. 9A, although shows another circumferential ablation catheter wherein the balloon has a tapered outer diameter.
Figure 9C:
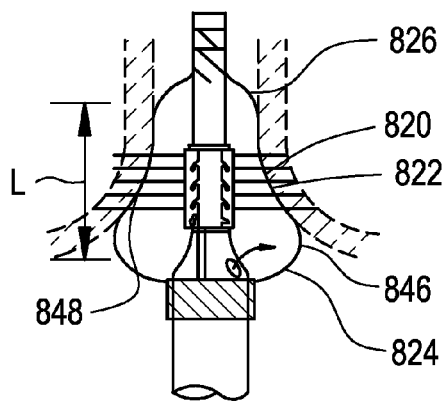
FIG. 9C shows a similar view to that shown in FIGS. 9A-B, although showing another circumferential ablation catheter wherein the balloon has a "pear"-shaped outer diameter with a contoured surface along a taper which is adapted to seat in the ostium of a pulmonary vein.

FIGS. 9A-C show various alternative embodiments of the present invention for the purpose of illustrating the relationship between the ultrasound transducer and balloon of the present invention just described above. More specifically, FIG. 9A shows the balloon (820) having "straight" configuration with a working length L and a relatively constant diameter X between proximal and distal tapers (824, 826). As is shown in FIG. 9A, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon (820).

The balloon (820) in FIG. 9A is also concentrically positioned relative to the longitudinal axis of the elongate catheter body (802). It is understood, however, that the balloon can be asymmetrically positioned on the elongate catheter body, and that the ablation device can include more than one balloon.

FIG. 9B shows another assembly according to the invention, although this assembly includes a balloon (820) that has a tapered outer diameter from a proximal outer diameter $X_1$ to a smaller distal outer diameter $X_2$. (Like reference numerals have been used in each of these embodiments in order to identify generally common elements between the embodiments.) According to this mode, this tapered shape is believed to conform well to other tapering regions of space, and may also be particularly beneficial for use in engaging and ablating circumferential paths of tissue along a pulmonary vein ostium.

Figure 9D:
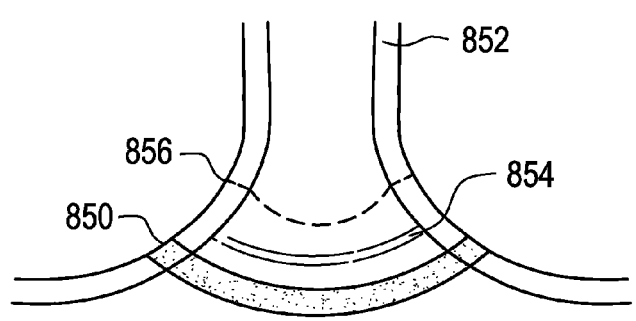
FIG. 9D shows a cross-sectional view of one circumferential conduction block which may be formed by use of a circumferential ablation catheter such as that shown in FIG. 9C.

FIG. 9C further shows a similar shape for the balloon as that just illustrated by reference to FIG. 9B, except that the FIG. 9C embodiment further includes a balloon (820) and includes a bulbous proximal end (846). In the illustrated embodiment, the proximate bulbous end (846) of the central region (822) gives the balloon (820) a "pear"-shape. More specifically, a contoured surface (848) is positioned along the tapered working length L and between proximal shoulder (824) and the smaller distal shoulder (826) of balloon (820). As is suggested by view of FIG. 9C, this pear shaped embodiment is believed to be beneficial for forming the circumferential conduction block along a circumferential path of atrial wall tissue that surrounds and perhaps includes the pulmonary vein ostium. For example, the device shown in FIG. 9C is believed to be suited to form a similar lesion to that shown at circumferential lesion (850) in FIG. 9D. Circumferential lesion (850) electrically isolates the respective pulmonary vein (852) from a substantial portion of the left atrial wall. The device shown in FIG. 9C is also believed to be suited to form an elongate lesion which extends along a substantial portion of the pulmonary vein ostium (854), e.g., between the proximal edge of the illustrated lesion (850) and the dashed line (856) which schematically marks a distal edge of such an exemplary elongate lesion (850).

As mentioned above, the transducer (830) can be formed of an array of multiple transducer elements that are arranged in series and coaxial. The transducer can also be formed to have a plurality of longitudinal sectors. These modes of the transducer have particular utility in connection with the tapering balloon designs illustrated in FIGS. 9B and 9C. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer (830) is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device (800) can also include additional mechanisms to control the depth of heating. For instance, the elongate catheter body (802) can include an additional lumen that is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon (820) can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer (830) may be mounted on a torquable member that is movably engaged within a lumen that is formed by the elongate catheter body (802).

The embodiments just described are believed to be particularly useful in catheter assemblies that are specifically adapted for ablating tissue along a region where a pulmonary vein extends from a left atrium in the treatment of atrial fibrillation. Therefore, the assemblies and methods of the present invention are also contemplated for use in combination with, or where appropriate in the alternative to, the various particular features and embodiments shown and described in the following U.S. patents that also address circumferential ablation at a location where a pulmonary vein extends from an atrium: U.S. Pat. No. 6,024,740 for "CIRCUMFERENTIAL ABLATION DEVICE ASSEMBLY" to Michael D. Lesh et al., on Feb. 15, 2000; U.S. Pat. No. 6,012,457 for "DEVICE AND METHOD FOR FORMING A CIRCUMFERENTIAL CONDUCTION BLOCK IN A PULMONARY VEIN" to Michael D. Lesh, on Jan. 11, 2000; U.S. Pat. No. 6,117,101 for "CIRCUMFERENTIAL ABLATION DEVICE ASSEMBLY" to Chris J. Diederich et al., on Sep. 12, 2000; U.S. Pat. No. 6,652,515 for "TISSUE ABLATION DEVICE ASSEMBLY AND METHOD FOR ELECTRICALLY ISOLATING A PULMONARY VEIN OSTIUM FROM AN ATRIAL WALL" to Maguire et al., on Nov. 25, 2003; and U.S. Pat. No. 6,500,174 for "CIRCUMFERENTIAL ABLATION DEVICE ASSEMBLY AND METHODS OF USE AND MANUFACTURE PROVIDING AN ABLATIVE CIRCUMFERENTIAL BAND ALONG AN EXPANDABLE MEMBER" to Maguire et al., on Dec. 31, 2002. The disclosures of these references are herein incorporated in their entirety by reference thereto. Where use according to an "over-the-wire" delivery mode is herein shown and described, it is further contemplated that other delivery modes such as the deflectable steerable modes described above may also be used.

Figure 10:
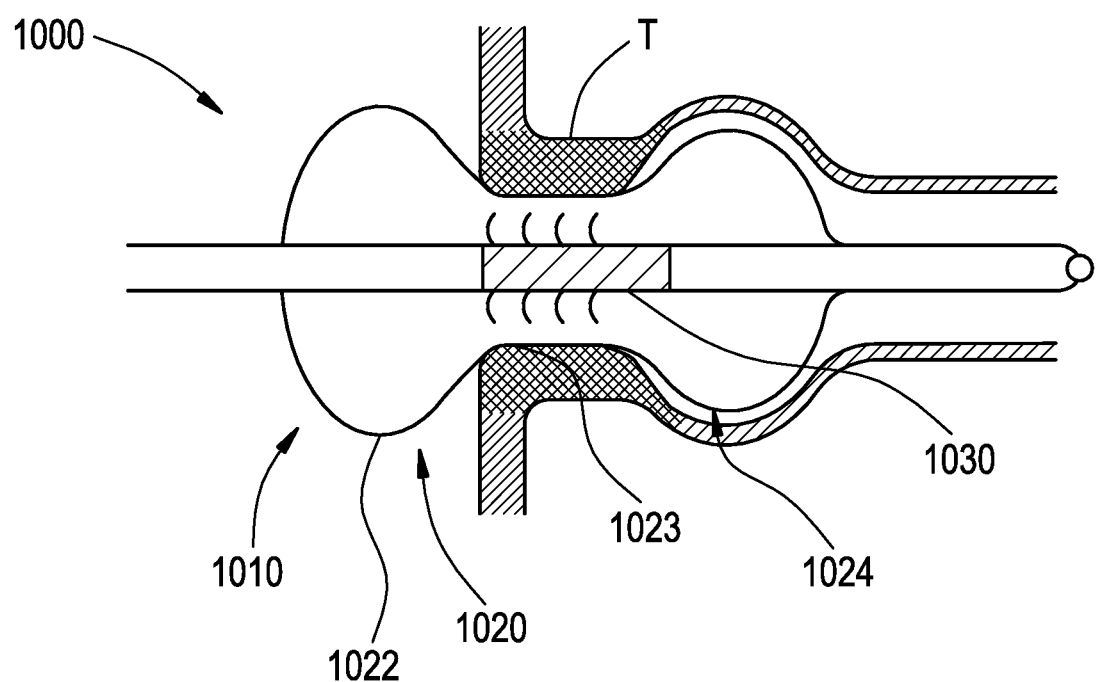
FIG. 10 shows a further shape for an expandable member according to the tissue ablation devices and procedures according to the invention.

Pulmonary veins have also been observed to present a thickened cuff of tissue at their respective ostia. This thickened cuff is believed to present a unique resistance to expansion of an expandable member with a working length extending from the atrium, across the ostia, and into the more compliant vein adjacent the ostium. Therefore, one embodiment of the invention further contemplates an expandable balloon having a shape with a waist that assists the balloon to seat at the thickened, less compliant ostium and position the ablative circumferential band of the ablation assembly there. Such an embodiment is shown in FIG. 10, wherein device (1000) is shown with a circumferential ablation member (1010) having an expandable member (1020) that is a balloon with a narrowed waist (1023) between two larger end portions (1022, 1024) of the working length. As shown, distal end portion (1024) of the balloon's working length expands with the vein wall, and proximal end portion (1022) of the balloon's working length expands to a relatively large outer diameter as the ostium becomes atrium. However, waist (1023) with its reduced diameter allows the assembly to seat at the thicker ostium with ablation element (1030) well positioned to ablatively couple through expandable member (1020) and into the circumferential region of tissue along the ostium.

Various particular material constructions may be used for a balloon such as just described for FIG. 10, in addition to particular ablation element/expandable member configurations, and still benefit by the "peanut" or waisted balloon shape with regards to pulmonary vein ostium ablation. In particular with regards to material construction, either a substantially compliant or elastomeric balloon material, or a substantially non-compliant or non-elastomeric variety may be used. Alternatively, a combination balloon construction with elastomeric/compliant and non-elastomeric/non-compliant regions along the working length, such as herein described, may be suitable.

Balloon shape is one factor that can enhance the balloon's ability to provide simultaneous anchoring as well as localized ablation. In another embodiment of the invention, a dumbbell shaped balloon having proximal and distal bulbs of different diameters may also be used. FIGS. 11A through 11E illustrate various views of a dumbbell shaped balloon having bulbous sections of different diameters according to one embodiment of the present invention.

Turning to FIG. 11A, the dumbbell shaped balloon (1100) consists of a single component comprised of two bulb sections, proximal bulb (1105) and distal bulb (1110), separated by a longitudinal mid-section (1115). The distal bulb (1110) is intended to anchor the balloon (1100) (and therefore, the ablation device) in a target vessel to facilitate ablation at a location. The proximal bulb (1105) is used to properly locate the ablation element for ablating the tissue at the location. In a preferred embodiment of the invention, the proximal bulb (1105) may also be used to house the ablation element. The mid-section (1115) is sized to most advantageously separate the bulb sections (1105, 1110) based on the anatomy of the body space to ablate. For example, when ablating in or around the atrial chamber or pulmonary vein ostium, the distal bulb (1110) may anchor the device in the pulmonary vein, while the proximal bulb (1105) locates the ablation element to ablate at the pulmonary vein ostium or atrial back wall. The distal bulb 1110 is therefore designed with a smaller diameter than the proximal bulb 1105 to reflect the atrial anatomy of the pulmonary vein and ostium, respectively.

As described above, various compliant, non-compliant or semi-compliant materials may be used for the balloon construction. Alternatively, various combinations of compliant, non-compliant or semi-compliant materials may be suitable. Where the ablation is to take place in the atrial chamber and/or around the pulmonary vein ostium, a preferable balloon will be constructed from a silicone and formed as a single unit utilizing a dip molding or liquid injection molding (LIM) process. However, this material is not meant to limit the scope of the invention, and other suitable semi-compliant materials, such as polyurethanes, or non-compliant materials, such as nylon may also be used individually or in combination thereof. Still other materials may be used as understood by one of skill in the art.

Where the ablation device is used to ablate tissue in the pulmonary vein, pulmonary vein ostium, or atrial chamber back wall, the distal bulb (1110) is sized to anchor in the pulmonary vein. In one embodiment, a distal bulb (1110) having an outside diameter before inflation of between 0.170 and 0.200 inches, and a working length (1) of between 0.115 and 0.125 inches has been found to be acceptable to anchor the balloon (1100) in place when expanded at least 300% at 3 atmospheres of pressure. It should be noted that the contemplated inflation pressure and final outside diameter defines the starting wall thickness of the bulb section. Most preferably, a distal bulb (1110) having a diameter of 0.180 inches±0.002 inches, and a working length (1) of 0.121±0.003 inches before inflation has been found to be acceptable.

During atrial ablation, the proximal bulb (1105) containing the ablation element is preferably located at the pulmonary vein/atrium interface, most preferably at the pulmonary vein ostium. This will allow the ablation element to ablate tissue within the ostium, or at the ostium along the atrial back wall. To properly locate the ablation element a proximal bulb (1105) having an outside diameter before inflation of between 0.250 and 0.300 inches, and a working length (1) of between 0.200 and 0.300 inches has been found to be acceptable. Most preferably, a proximal bulb (1105) having a diameter of 0.265 inches±0.002 inches, and a working length (1) of 0.265±0.002 inches before inflation has been found to be acceptable.

To facilitate placement and anchoring, it may be desirable to sequence the inflation of the proximal and distal bulb sections, (1105, 1110) respectively. For example, it may be desirable to anchor the ablation device in a pulmonary vein by expanding the distal bulb section (1110) before attempting to fully inflate the proximal bulb (1105) and locate the ablation element. This may be accomplished by having the proximal bulb section (1105) and distal bulb section (1110) chambered separately, with each separate bulb section (1105, 1110) having its own separate inflation lumen and inflation media source as earlier described. In a preferred embodiment, the proximal bulb (1105) and distal bulb (1110) sections are part of the same chamber having a single inflation lumen and inflation media source as illustrated in FIG. 11A. Sequencing inflation of the proximal bulb section (1105) and distal bulb section (1110) forming a single chamber may, for example, be accomplished by providing bulbs of different wall thickness.

FIGS. 11B and 11C are cross-sectional views of the proximal and distal bulbs (1105, 1110) respectively, illustrating the different bulb wall thickness. As shown in the Figures, the distal bulb (1110) is designed with a wall thickness (t) that is smaller than the proximal balloon bulb (1105) wall thickness (t'). This difference in thickness is sufficient to encourage inflation of the distal bulb (1110) before the proximal bulb (1105) is substantially inflated. In a preferred embodiment where the balloon is constructed from silicone and being used for atrial ablation, a proximal bulb (1105) having a wall thickness (t') of between 0.020 and 0.030 inches, and preferably 0.025±0.003 inches, before inflation has been found to be acceptable. Similarly, a distal bulb (1110) having a wall thickness (t) of between 0.010 and 0.020 inches, and preferably 0.015±0.003 inches before inflation, has been found to be acceptable.

The smaller wall thickness (t) results in the distal bulb (1110) exhibiting less radial resistance during inflation. Accordingly, as the balloon (1100) is filled with inflation fluid, the distal bulb (1110) starts to expand and inflate earlier than the proximal bulb (1105). As the distal bulb (1110) inflates and anchors in place, inflation fluid pressure increases, thus allowing the proximal bulb (1105) with its greater wall thickness (t') to commence inflation.

As earlier disclosed, the mid-section (1115) is sized to most advantageously separate the bulb sections (1105, 1110) based on the anatomy of the body space to ablate. For a silicone balloon (1100) used to ablate at the pulmonary vein/atrium interface, a mid-section having a working length before inflation of between 0.100 and 0.200 inches, and preferably between 0.120 and 0.150 inches has been found to be acceptable. To provide the necessary stiffness and radial resistance to inflation, this mid-section (1115) may have a wall thickness (t") of between 0.020 and 0.050 inches, and preferably 0.028±0.004 inches. The mid-section (1115) is shown in cross-section in FIG. 11C.

It should be understood that the dimensions describing the proximal and distal bulbs (1105, 1110) respectively and mid-section (1115), before inflation, including the proximal and distal bulb wall thickness (t', t) and mid-section wall thickness (t"), represent particular element sizes before the balloon (1100) is folded or crimped down onto a delivery member.

The proximal and distal bulbs (1105, 1110) may also be sequenced during inflation by varying material. By way of example, the distal anchor (1110) may be constructed from a compliant material, such as silicon, while the proximal bulb (1105) is constructed from a compatible but slightly less compliant or semi-compliant material, such as polyurethane. The recitation of these materials is exemplary, and one of skill in the art would understand that other combinations of compliant, semi-compliant and/or non compliant materials may also be used. As the single chamber balloon (1100) is inflated, the distal bulb (1110) with respond to the pressure induced by the inflation media more quickly than the less compliant proximal bulb (1105).

Another contact member design capable of enhancing the medical device's ability to provide simultaneous anchoring as well as localized ablation is illustrated in FIGS. 12A through 12D. This configuration utilizes an expandable member consisting of a single balloon chamber having a single bulbous configuration, but relies on differing wall thickness along the balloon surface to control the inflation size, and consequently shape. This allows the deployed balloon to expand into a configuration that more preferably adapts to the anatomical features of the target body space. A pear shaped bulbous balloon is shown for the purpose of example, as this shape seems to be desirable to anchor the medical device in the pulmonary vein for ablating the surrounding area, that is to say the pulmonary vein, the ostium, and/or atrium back wall. However, one of skill in the art would understand that other balloon shapes are contemplated based on the body space features of the target site, such as bulb, ball, egg or similar shapes that are mostly determined by the length, start diameter and wall thickness of the balloon.

As described above, medical balloons are typically made from an elastic material, such as silicone, that can stretch when the balloon inner chamber is subjected to internal pressures Pi greater than the pressure outside the balloon Po. This expansion ability is often used to facilitate anchoring the balloon in a desired location for ablation. The disclosed design concept utilizes the inflated shape and expansion rate of different regions of the bulbous chamber by varying the wall thickness of the balloon in the different regions. The net effect is a balloon that inflates first in the distal region to anchor in the pulmonary vein and second in the proximal region to serve as a transmission window for the ablation element.

Figure 12A:
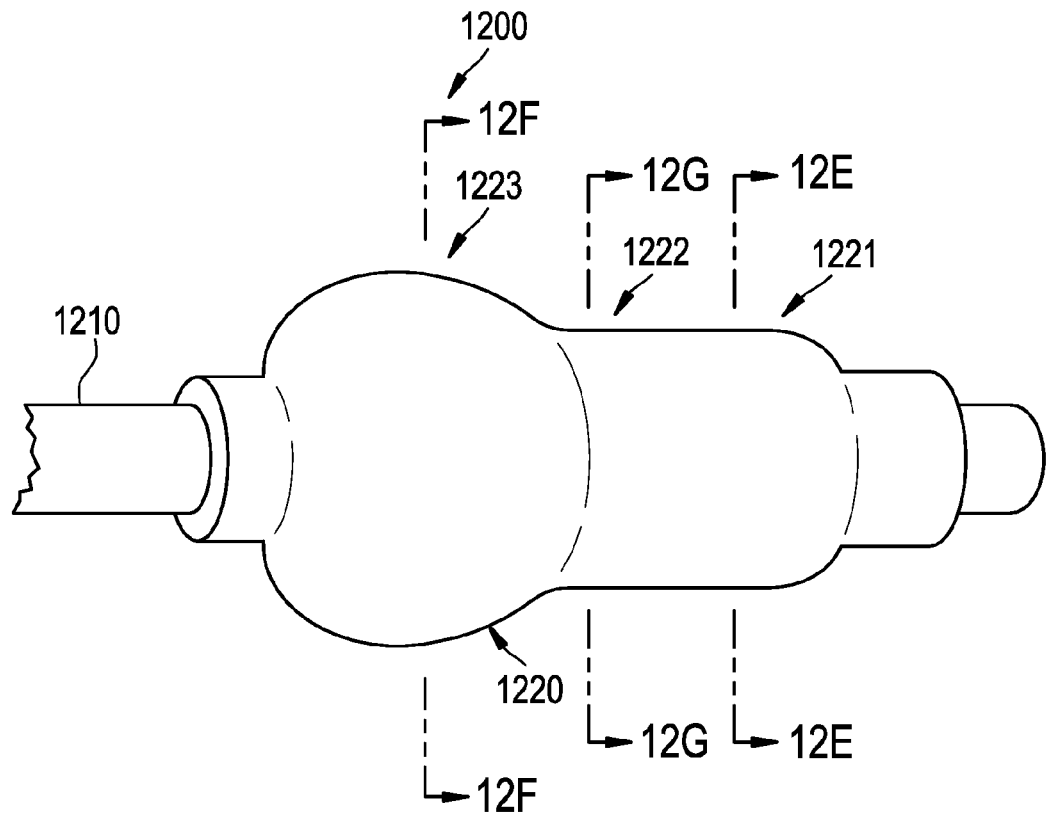
FIG. 12A is a perspective view showing a partially inflated expandable member consisting of a single balloon chamber have a single bulbous configuration according to one embodiment of the present invention.

FIG. 12A is a perspective view showing a medical device 1200 having a balloon 1220 in the initial un-inflated position. It should be understood that medical balloons are typically cut or formed to a particular size and folded and/or constrained around an elongate body in a low profile for delivery through the body vasculature. Once the balloon is delivered to the target location, it is inflated for deployment. The inflation of the balloon 1220 for the purpose of illustration can be described as a two-stage process—initial inflation and full inflation. However, in real-time, the clinician may inflate the balloon in one step and go directly from constrained through initial inflation to full inflation.

For the purpose of this description, initial inflation is defined as the point when the balloon 1220 is inflated to assume its unconstrained originally formed size and shape. That is to say, the pressure inside the balloon (Pi) is equal to the pressure outside the balloon (Po). Furthermore, the expanded inflation of the balloon 1220 is defined as the point when the pressure in the balloon Pi is greater than pressure outside the balloon Po. Relying on the elastic or "stretchability" of the balloon material, it should be understood that the greater the internal balloon pressure Pi, the greater the balloon 1220 can expand. Typically, medical balloons can experience internal pressures that are between 100 and 1100 percent of the external pressure Po. In a preferred embodiment of the present invention, the balloon 1220 can inflate and sufficiently anchor the distal section of the balloon 1220 when the internal pressure Pi is approximately 300 percent of the external pressure Po.

Returning to FIG. 12A, the medical device 1200 comprises a single chamber medical balloon member 1220 mounted along the distal end of an elongate body 1210 at proximal and distal bond points 1205, 1205' respectively. In a preferred embodiment, elongate body 1210 is a catheter as earlier described. The balloon 1220 illustrated has a single bulbous section, including a narrow tubular region 1221 located along the distal portion of the balloon, and a large spherical region 1223 located along the proximal portion of the balloon. For ablation in and around the regions surrounded by the pulmonary vein, the narrow distal region 1221 is sized to enter and anchor into the pulmonary vein. In one embodiment of the invention, a distal region 1221 having an outside diameter of between 0.170 and 0.200 inches after initial inflation has been found to be acceptable. The large spherical region 1223 is designed to expand and abut the pulmonary vein ostium and atrial back wall.

In addition, the spherical region 1223 may house the ablation device. During atrial ablation, the region 1223 containing the ablation element is preferably located at the pulmonary vein/atrium interface, most preferably at the pulmonary vein ostium. This will allow the ablation element to ablate tissue within the ostium, or at the ostium along the atrial back wall. To properly locate the ablation element a spherical region 1223 having an outside diameter before inflation of between 0.05 and 0.30 inches, and a working length (l) of between 5 mm and 100 mm inches has been found to be acceptable. Most preferably, a spherical region 1223 having a diameter between 0.10 and 0.20 inches, and a working length (l) between 20 mm and 60 mm inches before inflation has been found to be acceptable.

The balloon 1220 also has a rib 1222 located between the proximal and distal regions 1223 and 1221 respectively. The rib 1222 has a thickened section, seen in the sectional views illustrated in FIGS. 12B and 12D. This thickened section acts as a "belt", and provides resistance to balloon expansion as internal pressure (Pi) is increased. This "belting" prevents the bulbous balloon 1220 from forming a spherical or conical shape, which tends to cause the balloon 1220 to dislodge from the anchored position as it inflates. FIG. 12D clearly illustrates the belting provided by rib 1222 when the balloon 1220 is inflated. In addition, the belting provides an area for surrounding tissue to divert when the proximal and distal region 1223 and 1221 inflate. The tissue "packing" allowed by this diversion further anchors the balloon 1220 in place.

The size of the rib section 1222 may vary for different anatomical locations. For pulmonary vein anchoring, a ribbed section 1222 having a having an outside diameter before inflation of between 0.050 and 0.30 inches has been found to be acceptable. Most preferably, a rib section 1223 having a diameter of between 0.10 and 0.20 inches before inflation has been found to be acceptable.

To facilitate placement and anchoring, it may be desirable to sequence the inflation of the distal tubular region 1221 and proximal distal region 1223. For example, it may be desirable to anchor the ablation device in a pulmonary vein by expanding the distal tubular region 1221 before attempting to fully inflate the proximal region 1223 and locate the ablation element. As described earlier, this may be accomplished by providing distal tubular region 1221 and proximal spherical region 1223 with different wall thickness.

Figure 12B:
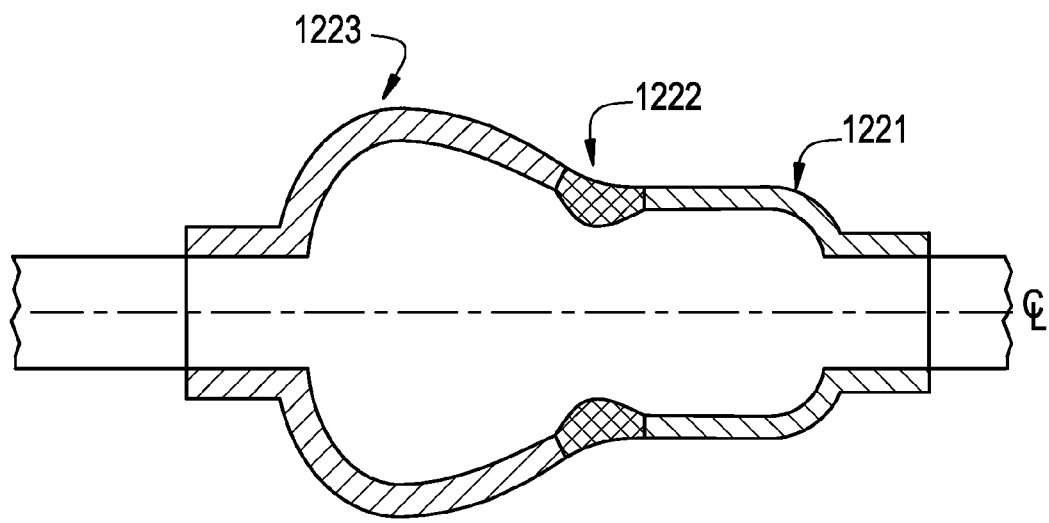
FIG. 12B is a section view showing a partially inflated expandable member consisting of a single balloon chamber have a single bulbous configuration according to one embodiment of the present invention.
Figure 12C:
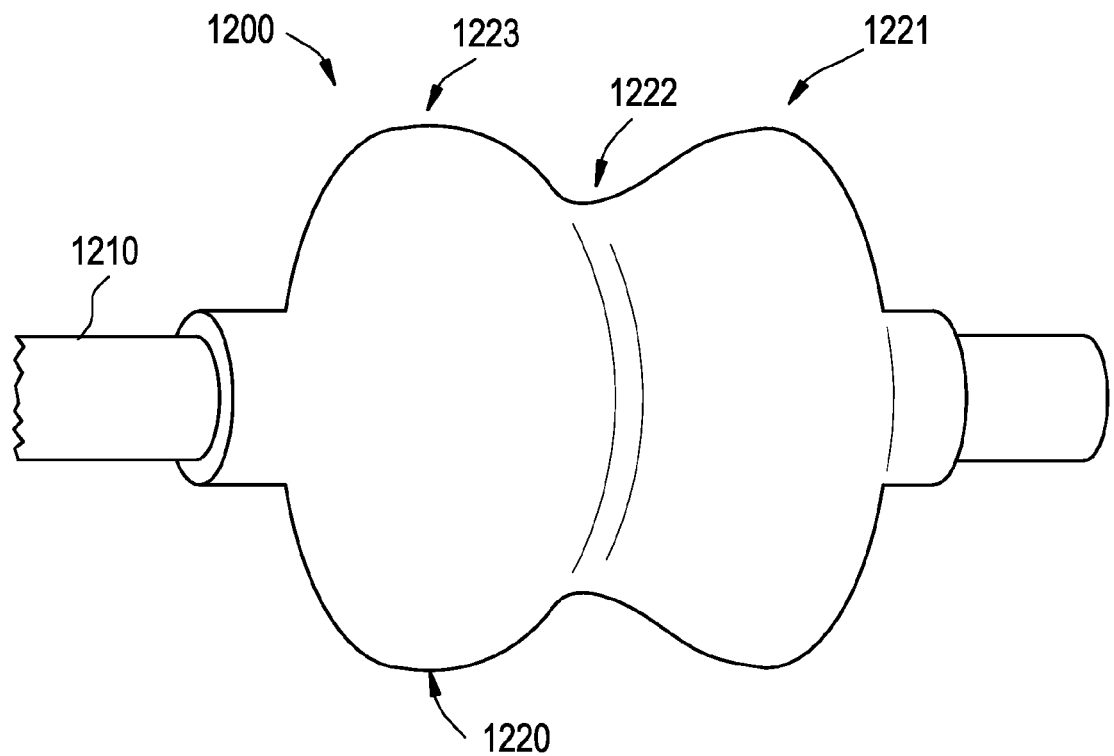
FIG. 12C is a perspective view showing a fully inflated expandable member consisting of a single balloon chamber have a single bulbous configuration according to one embodiment of the present invention.
Figure 12D:
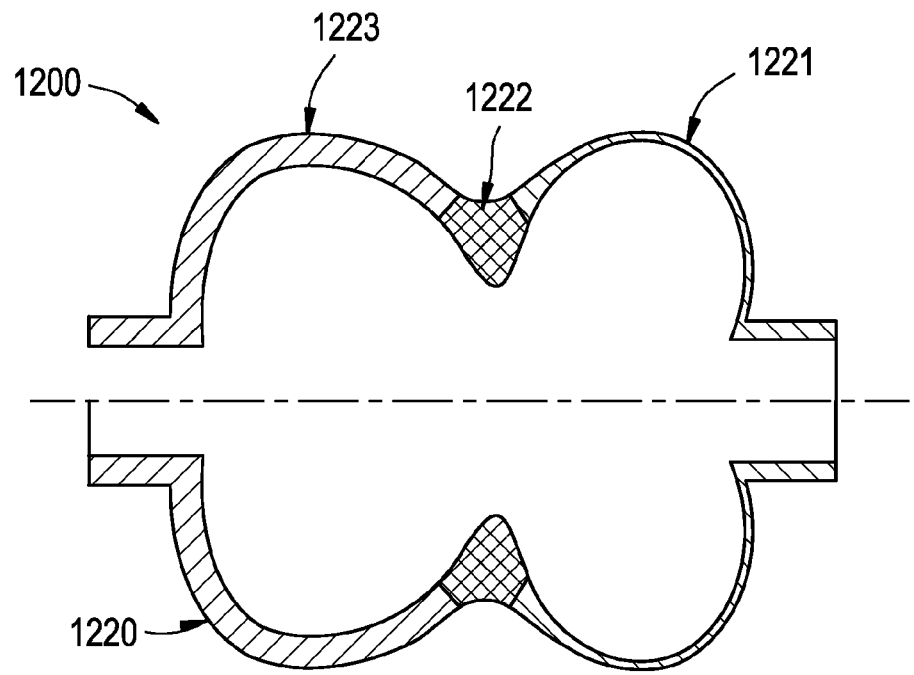
FIG. 12D is a section view showing a fully inflated expandable member consisting of a single balloon chamber have a single bulbous configuration according to one embodiment of the present invention.
Figure 12E:
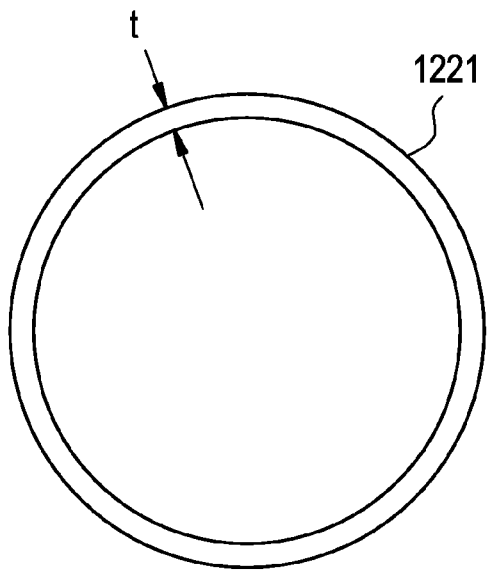
FIG. 12E is a cross-sectional view of the distal region of the expandable member according to one embodiment of the present invention.
Figure 12F:
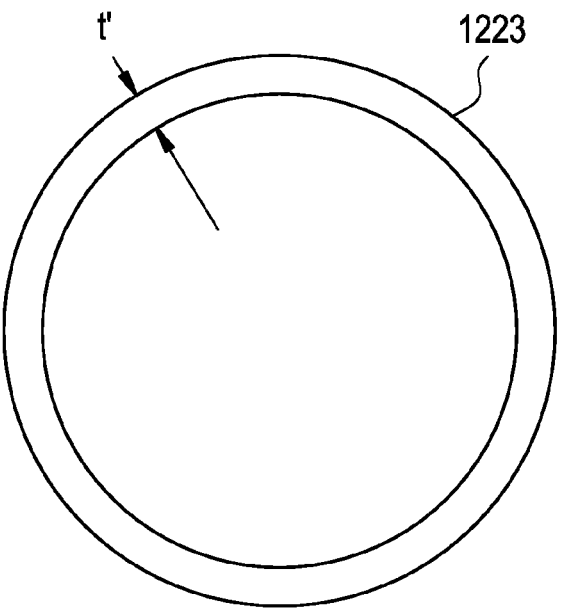
FIG. 12F is a cross-sectional view of the proximal region of the expandable member according to one embodiment of the present invention.
Figure 12G:
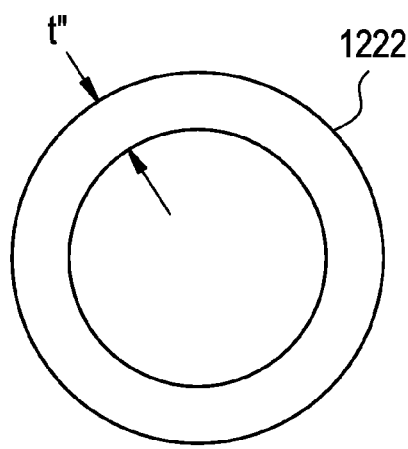
FIG. 12G is a cross-sectional view of the rib region of the expandable member according to one embodiment of the present invention.

FIGS. 12B and 12D are longitudinal cross-sectional views illustrating the distal tubular region 1221 and proximal region 1223 having different wall thicknesses. FIGS. 12E through 12G are diametric cross-sectional views illustrating the wall thickness of the distal tubular region 1221, proximal spherical region 1223 and rib 1222, respectively. As shown in the figures, the distal tubular region 1221 is designed with a wall thickness (t) that is smaller than the proximal spherical region 1223 wall thickness (t'). This difference in thickness is sufficient to encourage inflation of the distal tubular region 1221 before the proximal region 1223 is substantially inflated. In a preferred embodiment where the balloon is constructed from silicone and being used for atrial ablation, a distal tubular region 1221 having a wall thickness (t) of between 0.001 and 0.025 inches, and preferably 0.002 and 0.01 inches, before inflation has been found to be acceptable. Similarly, a proximal region 1223 having a wall thickness (t') of between 0.002 and 0.03 inches, and preferably between 0.003 and 0.012 inches before inflation, has been found to be acceptable.

The smaller wall thickness (t) results in the distal tubular region 1221 exhibiting less radial resistance during inflation. Accordingly, as the balloon 1200 is filled with inflation fluid, the distal tubular region 1221 starts to expand and inflate earlier than the proximal region 1223. As the distal tube 1221 inflates and anchors in place, inflation fluid pressure increases, thus allowing the proximal region 1223 with its greater wall thickness (t') to commence inflation.

As earlier disclosed, the rib along the mid-section 1222 is sized to prevent the bulbous balloon 1220 from assuming a spherical or conical shape, which may cause the balloon 1220 to self dislodge from a body space, such as the pulmonary vein, as it inflates. To provide the necessary stiffness and radial resistance to inflation i.e. belting, the rib along the rib region 1222 in silicone balloons may have a wall thickness (t") of between 0.004 and 0.035 inches, and preferably between 0.004 and 0.014 inches. The rib region 1222 is shown in cross-section in FIG. 12G.

It should be understood that the dimensions describing the distal tubular region 1221, proximal spherical region 1223, and ribbed region (1222), before inflation, including the associated wall thicknesses (t, t', and t"), represent particular element sizes before the balloon 1200 is folded or crimped down onto a delivery member.

The distal tubular region 1221 and proximal region 1223 may also be sequenced during inflation by varying the regions mechanical properties, such as tensile strength or elasticity. By way of example the various regions may be made from dissimilar materials, i.e., the distal tubular region 1221 may be constructed from a compliant material, such as silicon, while the proximal spherical region 1223 is constructed from a compatible but slightly less compliant or semi-compliant material, such as polyurethane. The recitation of these materials is exemplary, and one of skill in the art would understand that other combinations of compliant, semi-compliant and/or non-compliant materials may also be used.

Similarly, varying the tensile strength of the regions 1221 and 1223 may accomplished by other means. For example, the tensile strength of the tubular regions 1221 and 1223 may be varied by providing regions of dissimilar durometer, or by the addition of reinforcing elements, such as integrated fibers. In addition, the tensile strength of the region material may be differentiated by variation of the material density. One such method that can be employed to vary the material density is by creating a closed cell structure within the material.

As the single chamber balloon 1220 is inflated, the distal tubular region 1221 will respond to the pressure induced by the inflation media more quickly than the less compliant proximal region 1223, causing the tubular region 1221 to inflate earlier and anchor the balloon 1220 in a body orifice, such as the pulmonary vein.

Various device assemblies herein disclosed which provide an ablation balloon with an ablative circumferential band, in addition to the related methods of manufacture and use, are also considered applicable to modes other than the porous electrode type ablation element mode specifically described. For example, a band of thermally conductive material may be used in replacement of a porous material along the intermediate region of the balloon construction in order to form a thermal ablation element, and such features are considered useful with various of the disclosed embodiments such as for example with regard to the disclosed assemblies with elastomeric material only along the end portions of the working length, shapes for the respective expandable member having reduced diameter waists and/or tapers, etc. Moreover, the varied construction between the intermediate region and the end portions of the balloon according to those embodiments may also be applicable to an ultrasound ablation member, for example by varying the materials between these portions based upon their ultrasonically transmissive character, or for other purposes such as otherwise herein described.

The tissue ablation device assemblies of the invention also may include feedback control. For instance, one or more thermal sensors (e.g., thermocouples, thermisters, etc.) may be provided with the circumferential ablation device assemblies described, such as either on the outer side or the inside of the porous circumferential band for instance. Monitoring temperature at this location provides indicia for the progression of the lesion. The number of thermocouples may be determined by the size of the circumference to be ablated. If the temperature sensors are located inside the porous membrane, the feedback control may also need to account for any temperature gradient that occurs across the membrane. Furthermore, sensors placed on the exterior of the porous member may also be used to record electrogram signals by reconnecting the signal leads to different input port of the signal processing unit. Such signals can be useful in mapping the target tissue both before and after ablation.

In one embodiment, the temperature sensors comprise a thermocouple that is positioned about the outer side of the membrane along the circumferential band. In this location, the thermocouple lies on the outside of the band where it can directly contact the tissue-electrode interface. The thermocouples may also be blended into the outer surface of the ablation balloon in order to present a smooth profile. Transition regions which may be formed by either adhesive or melted polymer tubing, "smooth out" the surface of the ablation member as the surface steps up from the porous member outer surface to the thermocouple surface. Signal wires generally extend from the thermocouples to an electrical connector on the proximal end of the circumferential tissue ablation device assembly. The wires may be shielded. The thermocouple wires may extend along the catheter shaft longitudinally in a dedicated or shared lumen, or the wires can form a braided structure extending along the elongated body. The wires can also be routed proximally inside one or more tubes that extend parallel to and are attached to the elongated body. The wires can also be sewn into the wall along the circumferential band. These represent a few variations on various ways of routing the thermocouple wires to the proximal end of the tissue ablation device assembly.

Other feedback sensors and related assemblies, including for sensing ablation progression as well as position monitoring sensors and systems, are specifically contemplated in combination with the embodiments of this disclosure.

In addition, a circumferential ablation device assembly according to the present invention may be used in combination with other linear ablation assemblies and methods, and various related components or steps of such assemblies or methods, respectively, in order to form a circumferential conduction block adjunctively to the formation of long linear lesions, such as in a less-invasive "Maze"-type procedure. Examples of such assemblies and methods related to linear lesion formation and which are contemplated in combination with the presently disclosed embodiments are shown and described in the following U.S. patents: U.S. Pat. No. 5,971,983, issued on Oct. 26, 1999, entitled "TISSUE ABLATION DEVICE AND METHOD OF USE" filed by Michael Lesh, M. D. on May 9, 1997; U.S. Pat. No. 6,527,769 for "TISSUE ABLATION SYSTEM AND METHOD FOR FORMING LONG LINEAR LESION" to Langberg et al., on Mar. 4, 2003; and U.S. Pat. No. 6,522,930 issued on Feb. 18, 2003 entitled "TISSUE ABLATION DEVICE WITH FLUID IRRIGATED ELECTRODE", filed by Alan Schaer et al. on May 6, 1998. The disclosures of these references are herein incorporated in their entirety by reference thereto.

Other additional variations or modifications of the present embodiments that are not themselves specifically herein disclosed may be made by one of ordinary skill without departing from the scope of the present invention. For example, obvious variations or modifications to the detailed embodiments herein shown or described, including for example various combinations or sub-combinations among features of the detailed embodiments, may be made by one of ordinary skill based upon this disclosure and remain within the scope of the invention.

What is claimed is:

1. An ablation device assembly for ablating a circumferential region of tissue at a location within a body space where a pulmonary vein extends from an atrium, comprising: an elongate body with a proximal end portion, a distal end portion, and a longitudinal axis; an elastic contact member located along the distal end portion, the contact member having a circumferential wall and being expandable from a radially collapsed condition to a radially expanded condition, the contact member including a single chamber having a single bulbous section, the single bulbous section having a proximal region, a distal region and an intermediate region therebetween, a portion of the intermediate region having a thickened section along the circumferential wall, the thickened section configured to constrain a portion of the circumferential wall and prevent the single bulbous section from uniformly expanding and forming a spherical or conical shape when in the radially expanded condition; and an ablation element having an ablative energy source that is located along the distal end portion, wherein the ablation element cooperates with the contact member such that the ablative energy source emits a substantially circumferential pattern of energy through the circumferential wall.

2. The assembly of claim 1, wherein the contact member comprises an inflatable elastic balloon, the circumferential wall comprises an elastic outer skin of the balloon, and the ablative energy source is adapted to emit the circumferential pattern of energy through the outer skin of the balloon and into the circumferential region of tissue.

3. The assembly of claim 1, wherein the ablation element comprises a thermal ablation element.

4. The assembly of claim 1, wherein the ablation element comprises an ultrasound ablation element.

5. The assembly of claim 1, wherein the ablation element comprises a microwave ablation element.

6. The assembly of claim 1, wherein the ablation element comprises a cryoablation element.

7. The assembly of claim 1, wherein the ablation element comprises a fluid delivery element.

8. The assembly of claim 1, wherein the ablation element comprises a light emitting ablation element.

9. The assembly of claim 1, wherein the ablation element comprises an element that emits ionizing radiation.

10. The assembly of claim 1, further comprising a guidewire lumen along the distal end portion of the elongate body and which is adapted to slideably engage and track over a guidewire positioned within the body space.

11. The assembly of claim 10, wherein the guidewire lumen further comprises a guidewire passageway which extends along the elongate body between a proximal guidewire port located along the proximal end portion and a distal guidewire port located along the distal end portion.

12. The assembly of claim 1 wherein the elongate body is a steerable delivery member with a proximal end portion and a distal end portion that is deflectable and steerable by rotating the proximal end portion.

13. The assembly of claim 1, wherein the contact member further comprises a contoured elastic balloon that includes a balloon skin that forms the chamber and which is inflatable with an inflation medium in order to expand from the radially collapsed condition to the radially expanded condition.

14. The assembly of claim 1, wherein the contact member is constructed from the group of materials consisting of polyurethane, silicone, Mylar, latex, and combinations and blends thereof.

15. The assembly of claim 14, wherein the contact member exhibits at least about a 400% elastic expansion before yield.

16. The assembly of claim 14, wherein the contact member has a profile in the radially collapsed condition that is between about 0.060 and 0.200 inches, inclusive, and the expanded outer diameter is between about 0.25 and 1.5 inches, also inclusive.

17. The assembly of claim 1, wherein the elongate body further comprises: a fluid passageway extending between a proximal port, which is located along the proximal end portion and is adapted to couple to a pressurizeable fluid source, and a distal port, which is located along the distal end portion and through which the fluid passageway is fluidly coupled to the contact member.

18. The assembly of claim 1, further comprising an expansion actuator that is adapted to expand the expandable member from the radially collapsed condition to the radially expanded condition.

19. The assembly of claim 1 wherein the wall thickness of the distal region is smaller than the wall thickness of the proximal region.

20. The assembly of claim 1 wherein the distal region includes a narrow tubular section and the proximal region includes a large spherical section.

21. The assembly of claim 1 wherein the most distal circumferential region has different mechanical properties than the most proximal circumferential region.

22. An elastic contact member having a circumferential wall and being expandable from a radially collapsed condition to a radially expanded condition, the contact member including a single chamber having a single bulbous section, the single bulbous section having a proximal region, a distal region and an intermediate region there between, wherein the distal region and the proximal region have dissimilar tensile strengths, the intermediate region having a thickened section along the circumferential wall, the thickened section configured to constrain a portion of the circumferential wall and prevent the single bulbous section from uniformly expanding and forming a spherical or conical shape when in the radially expanded condition.

\* \* \* \* \*